(12) United States Patent
Biggs et al.

(10) Patent No.: US 6,301,970 B1
(45) Date of Patent: Oct. 16, 2001

(54) CUMULATIVE DAMAGE MODEL FOR STRUCTURAL ANALYSIS OF FILED POLYMERIC MATERIALS

(75) Inventors: Gary L. Biggs; John J. Nestor, III, both of Silver Spring, MD (US)

(73) Assignee: The United States of America the Secretary of the Navy, Washington, DC (US)

( * ) Notice: Subject to any disclaimer, the term of this patent is extended or adjusted under 35 U.S.C. 154(b) by 0 days.

(21) Appl. No.: 09/366,763

(22) Filed: Aug. 4, 1999

Related U.S. Application Data

(60) Provisional application No. 60/095,452, filed on Aug. 6, 1998.

(51) Int. Cl.[7] .................................................. G01N 19/00
(52) U.S. Cl. .............................................. 73/804; 73/789
(58) Field of Search ............................ 73/795, 789, 804, 73/806, 808, 809, 810, 811

(56) References Cited

U.S. PATENT DOCUMENTS

| | | | |
|---|---|---|---|
| 4,754,645 | * 7/1988 | Piche et al. | 73/597 |
| 5,531,123 | * 7/1996 | Henkel | 73/795 |
| 5,736,645 | * 4/1998 | Chin-Chan et al. | 73/799 |
| 5,764,068 | * 6/1998 | Katz et al. | 73/778 |

* cited by examiner

*Primary Examiner*—Benjamin R. Fuller
*Assistant Examiner*—Maurice Stevens
(74) *Attorney, Agent, or Firm*—Mark Homer

(57) ABSTRACT

A method of predicting fatigue failure in a filled polymeric material is provided. The method involves the calculation of stress at the region of highest stress using an equation which includes as parameters, regression coefficients of the stress vs. modulus obtained from a finite element analysis. Once the regression coefficients are obtained, there is no further need to perform a finite element analysis. The calculated stresses are numerically integrated in a damage equation using a Monte Carlo method, using a cumulative model to estimate when failure will occur. The method has been tested in the case of temperature stress loading of a solid propellant rocket motor.

21 Claims, 5 Drawing Sheets

AGEMOD SAMPLE INPUT FILE (comments on right)

```
     23     0.00    1.0    1.0        ! (num of pts, initial age, relax time, var frq)
             7.00   24.0    0.1   0.0
            60.00   18.0    4.0   0.0
             4.00   13.0    8.0   0.0
           730.00   18.0    4.0   0.0
             7.00   24.0    0.1   0.0   ! Time Interval-Temperature Profile
             2.00   13.0   10.0   0.0   ! (interval, temp, temp std dev, var amp)
          1460.00   23.0    0.1   0.0
             2.00   13.0   10.0   0.0
           180.00   18.0    4.0   0.0
             4.00   13.0    8.0   0.0
           730.00   18.0    4.0   0.0
(a)          7.00   24.0    0.1   0.0
             2.00   13.0   10.0   0.0
          1460.00   23.0    0.1   0.0
             2.00   13.0   10.0   0.0
           180.00   18.0    4.0   0.0
             4.00   13.0    4.0   0.0
           730.00   18.0    4.0   0.0
             7.00   24.0    0.1   0.0
             2.00   13.0   10.0   0.0
          1460.00   23.0    0.1   0.0
             2.00   13.0   10.0   0.0
           180.00   18.0    4.0   0.0
      9                                 ! (num of pts in following profile)
             0.00   66.0
            36.52   63.0
           146.10   62.0                ! Age-Stress Free Temperature Prof.
           292.20   61.0                  (age, stress free temperature)
(b)        438.37   60.0
           657.20   59.0
          1826.25   58.0
          3652.50   57.0
          7305.00   56.0
           66.0    25.0    0.080        ! (init TSF, amb. temp, std dev frac)
      8                                 ! (num of pts in following profile)
           -40.0    2.76
           -29.0    2.12
           -18.0    1.57
(c)         -7.0    1.07                ! Temp-Log10 Bulk Temp. Shift Profile
             7.0    0.52                  (temp, log10 Bulk Temp. Shift)
            25.0    0.03
            43.0   -0.57
            63.0   -1.06
      8                                 ! (num of pts in following profile)
           -40.0    4.27
           -29.0    3.66
           -18.0    2.50
(d)         -7.0    1.58                ! Temp-Log10 Int. Temp. Shift Profile
             4.0    0.60                  (temp, log10 Int. Temp. Shift)
            24.0    0.00
            43.0   -0.38
            65.0   -1.45
      8                                 ! (num of pts in following profile)
            -2.0    3.05
            -1.0    2.85
             0.0    2.70                ! Log10(t/aT)-Log10(Bulk Modulus)
(e)          1.0    2.55                ! Profile
             2.0    2.50                ! (log10(t/aT), log10(bulk modulus))
             3.0    2.40
             4.0    2.35
             5.0    2.30
      8                                 ! (num of pts in following profile)
            -2.0    3.60
```

Fig. 2A

|     |          |       |        |                                          |
|-----|----------|-------|--------|------------------------------------------|
|     | -1.0     | 3.45  |        |                                          |
|     | 0.0      | 3.30  |        |                                          |
|     | 1.0      | 3.20  |        | ! Log10(t/aT)-Log10(Intf. Modulus)       |
| (f) | 2.0      | 3.10  |        | ! Profile                                |
|     | 3.0      | 3.00  |        | ! (log10(t/aT), log10(intf. modulus))    |
|     | 4.0      | 2.90  |        |                                          |
|     | 5.0      | 2.80  |        |                                          |
|     | 6        |       |        | ! (num of pts in following profile)      |
|     | 1278.375 | 3.84  | 1.00   | ! Age-Kt Profile                         |
|     | 2118.450 | 3.31  | 10.00  | ! (age, Kt, stat wgt of data pt)         |
|     | 2337.600 | 1.82  | 5.00   |                                          |
| (g) | 2483.700 | 2.79  | 4.00   |                                          |
|     | 2739.375 | 2.23  | 12.00  |                                          |
|     | 2848.950 | 1.64  | 3.00   |                                          |
|     | 0.15     |       |        | ! (std dev of log10 (Kt) )               |
|     | 11       |       |        | ! (num of pts in following profile)      |
|     | 800.0    | 520.0 | 146.0  | ! Interface Modulus-Bulk Modulus         |
|     | 1450.0   | 320.0 | 163.0  | ! Stress Profile                         |
|     | 1150.0   | 560.0 | 225.0  | ! (intf. modulus,bulk modulus,stress)    |
|     | 1100.0   | 480.0 | 202.0  |                                          |
| (h) | 850.0    | 500.0 | 110.0  |                                          |
|     | 618.0    | 152.0 | 50.0   |                                          |
|     | 663.0    | 180.0 | 83.0   |                                          |
|     | 785.0    | 226.0 | 116.0  |                                          |
|     | 895.0    | 261.0 | 130.0  |                                          |
|     | 1102.0   | 298.0 | 167.0  |                                          |
|     | 2178.0   | 428.0 | 250.0  |                                          |
|     | -29.0    | 25.0  | 25.0   | ! (tempfe,bulk WLF Tref,intf. WLF Tref)  |
|     | 6        |       |        | ! (num of pts in following profile)      |
|     | 1278.375 | 3.22  |        | ! Age-log10 (Intf. Modulus) Profile      |
|     | 2118.450 | 3.26  |        | ! (age, log10(intf. modulus))            |
| (i) | 2337.600 | 3.09  |        |                                          |
|     | 2483.700 | 3.23  |        |                                          |
|     | 2739.375 | 3.20  |        |                                          |
|     | 2848.950 | 3.03  |        |                                          |
|     | 0.98     | 0.130 |        | ! (mean bulk mod. ratio,std dev bulk mod. ratio) |
|     | 1.12     | 450.0 |        | ! (maximum aging function,half-life of aging function) |
|     | 0.260    | 0.910 |        | ! (std dev log10(bulk aT),std dev log10(intf. aT)) |
| (j) | 0.031    | 0.077 |        | ! (std dev log10(bulk mod.),std dev log10(intf. mod.)) |
|     | 1.20     |       |        | ! (k3d)                                  |
|     | 20.0     |       |        | ! (sigma infinity)                       |
|     | 0.0006944|       |        | ! (tau0)                                 |
|     | 7        |       |        | ! (num of pts in following profile)      |
|     | 1278.375 | 1.982 | 12.00  | ! Age-log10 (sigma0) Profile             |
|     | 2337.600 | 2.078 | 20.00  | ! (age, log10(sigma0), data stat wgt)    |
|     | 2483.700 | 2.104 | 15.00  |                                          |
| (k) | 2739.375 | 2.180 | 6.00   |                                          |
|     | 2848.950 | 2.010 | 9.00   |                                          |
|     | 2848.950 | 2.093 | 23.00  |                                          |
|     | 3396.825 | 2.024 | 18.00  |                                          |
|     | 7        |       |        | ! (num of pts in following profile)      |
|     | 1278.375 | 7.44  | 10.00  | ! Age-B exponent Profile                 |
|     | 2337.600 | 8.74  | 15.00  | ! (age, B exponent, stat wgt of data)    |
|     | 2483.700 | 7.05  | 8.00   |                                          |
| (l) | 2739.375 | 9.88  | 4.00   |                                          |
|     | 2848.950 | 7.62  | 5.00   |                                          |
|     | 2848.950 | 9.60  | 2.00   |                                          |
|     | 3396.825 | 10.00 | 20.00  |                                          |
|     | 1.2      |       |        | ! (std deviation of B exponent)          |
|     | 100000   | -991  |        | ! (number of iterations, initial integer seed) |

Fig. 2B

CUMULATIVE DAMAGE MODEL FOR STRUCTURAL ANALYSIS OF FILED POLYMERIC MATERIALS

CLAIM OF PRIORITY

This application makes reference to, incorporates the same herein, and claims all benefits accruing under 35 U.S.C. §119 from our provisional application entitled CUMULATIVE DAMAGE MODEL FOR STRUCTURAL ANALYSIS OF FILLED POLYMERIC MATERIALS filed with the United States Patent and Trademark Office on Aug. 6, 1998 and there duly assigned Ser. No. 60/095,452.

BACKGROUND OF THE INVENTION

1. Field of the Invention

The present invention relates generally to a method of predicting the service life of filled polymeric materials.

2. Description of the Related Art

There are numerous situations in which it is important to be able to predict the fatigue failure of a filled polymeric material. Examples of filled polymeric materials in which fatigue failure is critical include airplane parts, rubber tires and solid propellant rocket motors. Since in many cases the polymer will have a long service life, perhaps on the order of years, it is desirable and often critical to be able to estimate the service life using mathematical models.

For example, in the case of solid propellant rocket motors, grain structural integrity can be the factor limiting the usable service life. If structural failure occurs, it is almost certain that ballistic performance will be substantially altered, possibly to the point of catastrophic motor failure. It is therefore desirable to be able to estimate what the chances of grain failure are as the motor is handled and stored prior to use.

In the case of solid propellant rocket motors, there are many modes by which the solid propellant within the rocket motor can receive a mechanical stress load. One of the most common is stress arising from thermal contraction. This particularly significant where the propellant is bonded to a steel pressure vessel. The propellant is typically cured at elevated temperatures to chemically accelerate the curing process. Since the coefficient of thermal expansion of the propellant is typically an order of magnitude greater than that of the steel vessel, and the Young's modulus of steel is roughly five orders of magnitude higher than that of the propellant, the propellant cannot contract fully upon cooling. This yields a rocket motor which is stress-free at the elevated temperature, but under continual stress once the rocket motor cools.

The modeling of stress in this situation is complicated as the propellant, in time, responds to this environment by undergoing changes at the molecular level that tend to relieve some of this stress. These changes generally consist of viscous flow of the polymeric binder and changes in crosslinking. These changes cause the propellant to take a permanent set, much as a garden hose which has been coiled in storage. This process is commonly referred to as a shift in the stress-free temperature.

While stressed, the binder microstructure also begins to tear. This process has been observed to increase linearly with time up to the point of macroscopic fracture when the applied stress is constant. The degree of damage, or damage fraction, done to the binder is therefore directly related to the total time the stress was applied and the time required to produce macroscopic failure at that same stress, specifically to the ratio of the former to the latter. At different levels of stress the amount of damage produced in a given amount of time varies considerably, being proportional to the stress raised to a large power, usually in the range of 6 to 12. If the propellant has been loaded to a number of different stresses, that is, has a complex service life history, the cumulative damage is simply the sum of each of the individual constant stress components. When they sum to unity, macroscopic failure is imminent.

The binder may also continue to undergo chemical changes long after the motor has been removed from its curing oven. These may include continued crosslinking chemical reactions with trace amounts of curative or reactions induced by exposure to the ambient environment, for example binder oxidation. Migration of mobile chemical species may produce non-homogeneous areas with the grain. These will frequently manifest themselves as changes in the propellant's mechanical properties which will in turn modify the level of stress, by changes in Young's modulus, or the strength, by changes in the maximum stress that can be attained.

To account for the inevitable cyclic nature of the loading in a complex sequence the linear cumulative damage model is often employed. As the name implies, there is a finite amount of damage sustained by the material during each segment of its load history. The damage contributions are numerically added, using a running total. Damage is conveniently expressed as a ratio, defined as the time dwelt under a constant load divided by the time required to produce failure at the same load level. When the sum of damage for a many-load sequence approaches unity, failure is imminent.

The level of stress within the structure must be known in order to estimate damage. This is usually determined by performing a finite element analysis. For complicated structures the corresponding finite element model may be quite large, requiring a significant amount of computation to exercise. If the load sequence is long and varied it may be necessary to make many runs of the finite element model to compute the corresponding stress sequence. For moderate to large finite element models, the time needed is often so large that it is not practical to perform the calculation. Rather, engineering judgments and approximations are sometimes made, so that many of the loads suspected of causing little or no damage are ignored. This is at best an imprecise process.

There is another complicating factor that is specifically associated with polymeric materials: the large statistical variability of the mechanical properties. Furthermore, when estimating the performance of a large population of structural members, the specific environment for each one may not be the same, but rather lies within some statistical distribution. These factors place a large uncertainty in the level stress applied within the structure throughout its service life. Because the amount of damage changes exponentially as the stress changes, this uncertainty in the stress magnitude is magnified in the results.

While the older models can accurately evaluate the amount of damage that occurs over a specific set of material properties and environmental conditions there has not been any provision to gauge the impact of their statistical variability. Although this could be done by simply repeating the analysis a number of times, using a statistical sample input for each and noting the incidence of failure and success, this has been not practical owing to the large amount of computational effort required. For structures with a relatively low failure rate, which is the usual case, the finite element model would need to be exercised thousands or even tens of thousands of times, that is, once for each load level within each load history, to estimate reliability. For a finite element model of any appreciable size this is not practical and practice is not done. Rapid and easy calculation of the fatigue life would be generally desirable, and would be particularly useful in a design process where the designer may have to produce numerous design iterations.

Methods to predict fatigue failure are seen in the following examples of the contemporary art. U.S. Pat. No. 5,531,123, to Henkel, entitled Remote and Powerless Miniature Fatigue Monitor and Method, describes a passive monitor for measurement of fatigue and a method for fatigue testing. The method includes locating a region of high stress, monitoring the fatigue in the direction of principal stress using a passive fatigue monitor during cycle loads, and using Miner's rule for cumulative damage to estimate fatigue life. This method, however, requires the identification of a high stress region and the experimental cycling of the material under loads to obtain fatigue data. This is an involved process which requires assumptions about the regions of high stress, and is in particular not practical for rapid estimation of fatigue life in a design process.

U.S. Pat. No. 5,736,645, to Chin-Chan et al., entitled Method of Predicting Crack Initiation Based Fatigue Life, describes a method involving plotting the finite element stress states of a stress history for a given component at a predetermined critical location in the stress space and determining the least square fit ellipsoid of the stress states. This method attempts to overcome the problems of uniaxial fatigue analysis by performing a multiaxial fatigue analysis. We have found that this method does not address many of the problems associated with filled polymeric materials, however.

"Problem of the Month, July 1997—Monte Carlo Reliability Model Starting With WinSMITH Weibull Data", originating with Barringer and Associates, Inc., describes a method for estimating the fatigue life of a pressure vessel (coke drum). The method involves obtaining stress data, building (modeling) the stress distribution, simulating stress using a Monte Carlo approach and the use of Miner's rule for fatigue. This example illustrates the use of the Miner's rule assumption that when the sum of damage for a many-load sequence approaches unity, failure is imminent. In this example, though, a model having actual experimental stresses and the S-N curve was available, and a complete finite element analysis was not necessary for each cycle. We have noticed this example therefore does not address the problems encountered in using a Monte Carlo approach with filled polymeric materials.

We have discovered, then, that what is needed is an improved, more rapid method of estimating the probability of fatigue failure in filled polymeric materials.

SUMMARY OF THE INVENTION

It is therefore an object of the present invention to provide an improved method of estimating fatigue life of polymeric materials.

It is a further object of the invention to provide a more rapid method of estimating fatigue life of polymeric materials.

It is yet further object of the invention to provide a more accurate method of estimating fatigue life of polymeric materials.

It is still further object of the present invention to provide a method of estimating fatigue life of polymeric materials which does not rely on engineering judgments ignoring the loads suspected of causing little or no damage.

It is still yet further object of the present invention to provide a method of estimating fatigue life of polymeric materials which can be performed on a personal computer or workstation.

It is another object of the present invention to provide a method of estimating fatigue life of polymeric materials which allows rapid testing of design iterations.

It is yet another object of the present invention to provide a method of estimating fatigue life of polymeric materials which is less expensive.

It is still another object of the present invention to provide an improved method of estimating the fatigue life of solid propellant rocket motors.

The present invention provides a method for estimating the fatigue damage to a filled polymeric material, including the steps of obtaining mechanical data necessary for performing a finite element analysis; exercising a finite element model over the range of mechanical property values that will be encountered in use; determining the area of highest stress in the filled polymeric material; performing a regression analysis versus the input modulus for the region of peak stress; performing a numerical integration for a given load history to which the structure of interest is exposed, with stress being determined based on the results of the regression analysis; and performing a Monte Carlo simulation involving load conditions and the values for parameters describing the material and structure.

BRIEF DESCRIPTION OF THE DRAWINGS

A more complete appreciation of the invention, and many of the attendant advantages, thereof, will be readily apparent as the same becomes better understood by reference to the following detailed description when considered in conjunction with the accompanying drawings in which like reference symbols indicate the same or similar components, wherein:

FIGS. 2(a) and (b) are a sample input file for a computer program performing the present invention;

DESCRIPTION OF THE PREFERRED EMBODIMENTS

The contents of our provisional application Ser. No. 60/095,452, entitled CUMULATIVE DAMAGE MODEL FOR STRUCTURAL ANALYSIS OF FILLED POLYMERIC MATERIALS, filed with the United States Patent and Trademark Office on Aug. 6, 1998 are herein incorporated by reference.

The present invention provides a method which is a flexible engineering tool which may be used for many different loading histories and material property sets. Examples will be provided illustrating the use of the method for estimating the probability of solid propellant structural failure, to thereby predict the service life of the motor, but the method may be applicable to estimating the service life of other filled polymeric materials and devices.

Figure 1:
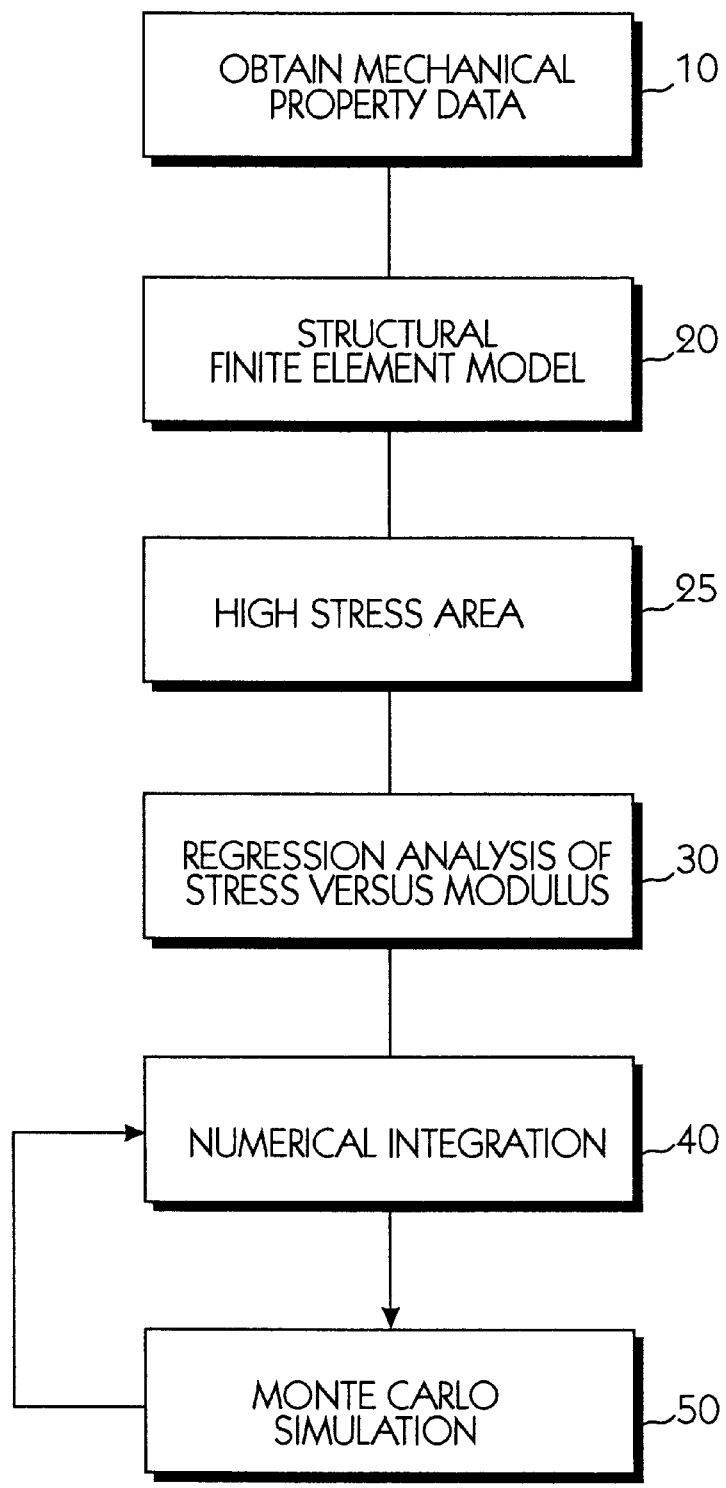
FIG. 1 is a flow diagram illustrating the general method suitable for the practice of the present invention.

FIG. 1 is a flow diagram illustrating the general method of the present invention for estimating fatigue damage. In step 10, the mechanical properties data necessary for performing a finite element analysis are obtained. If necessary, these may be obtained experimentally from samples of the materials used.

In step 20, a finite element model is exercised over the range of mechanical property values that will be encountered in use. Specifically, the load history is examined to determine the maximum and minimum values of relaxation modulus that will be encountered. The relaxation modulus is derived from the loading time and temperature.

In step 25, the area of highest stress is determined and selected from the finite element model. The area of highest stress may be determined from the finite element model, or may be determined from full scale overload testing of the structure. In step 30, a regression analysis is performed versus the moduli input into the finite element model, to determine regression coefficients as discussed below.

In step 40, numerical integration is performed for a given load history profile to which the structure of interest is exposed. For example, this profile could represent loads experienced during times in storage, shipment and handling. Commonly, the load history is a time-temperature profile.

In step 50, a Monte Carlo simulation is performed. The Monte Carlo simulation involves a statistically random selection of values for the load conditions and for the parameters describing the material and structure, as described below. These values are used in the numerical integration of step 40, and numerous iterations of the numerical integration are general performed.

In the present invention, the stress, $\sigma$, at the area of interest is determined using the following formula:

$$\sigma = K \sum_{i=1}^{N} (a_i E_{ni} E_i)(T_{SF} - T)/(T_{SF0} - T_0) \quad (1)$$

Here, $E_i$ are the relaxation moduli (for example Young's moduli) of the materials composing the structure (N=1 for a single, isotropic material); $E_{ni}$ are aging functions for determining the effect of aging of the material on the relaxation modulus; variables $a_i$ are regression coefficients for estimating the stress at a particular point in a specific structure; K is a proportionality constant for approximating the three-dimensional stress field; $T_{SF}$ is the stress-free temperature; $T_{SF0}$ is the common stress-free temperature at which the $a_i$ were derived, and may be equal to the initial stress-free temperature, before permanent set has occurred; $T_0$ is the common environmental temperature at which the $a_i$ were derived; and T is the temperature at which the stress $\sigma$ is being estimated.

The relaxation moduli $E_i$ are experimentally determined values from mechanical properties tests. They may be determined, for example, from standard JANNAF-class specimens.

The aging parameters $E_{ni}$ are determined by comparing aged samples of the materials to unaged samples, and may be derived from a regression analysis of the aged sample data. The time-dependent aging function may include the approximation that the aging function has a constant value for ages older than the last measured datum. The approximation avoids errors which may arise from extrapolating the aged sample data past the last datum. The aging parameters are normalized to have a value of unity for unaged material.

The regression coefficients $a_i$ allow for the estimation of the stress in a particular structure without performing a finite element analysis for every iteration. These coefficients are determined by exercising a finite element model of the structure over the range of mechanical property values that will be encountered in use for the relevant load mechanism, which may be thermal, shock, vibration, etc. A regression analysis is then performed to find the values of $a_i$ which force the equation to reproduce the finite element results at the peak structural load location.

The proportionality constant, K, is a factor to adjust for the three dimensional geometry of the structure. It is used to compensate for the ratio of maximum structural stress to that predicted when a two-dimensional finite element analysis is used to determine the values of $a_i$.

The value of K may be equal to unity if the working finite element model is sufficient to fully model the structure of interest. However, if, for example, the working model is two-dimensional (2-D), but the physical situation demands a three-dimensional (3-D) description, then a three-dimensional model may be constructed and exercised to determine the magnitude of the 3-D effect. This result is used to modify the 2-D result by means of the factor K.

Polymeric materials may undergo an internal tearing process when subjected to a sustained load. This damage process continues until macroscopic failure occurs. The stress calculated in equation 1 may be used to determined fatigue damage to the structure. Once the parameters of equation 1 have been determined, further use of the finite element model for the structure is unnecessary. In the present invention, damage, D, is calculated by performing a numerical integration of the formula equation:

$$D = ([\sigma_0 - \sigma_\infty]^B t_o)^{-1} \int ([\sigma(t) - \sigma_\infty]^B / a_T(t)) dt \quad (2)$$

Here, the parameter $\sigma_0$ is the stress that will cause failure $t_0$. $\sigma_\infty$ is the threshold stress below which failure will not occur irrespective of load time. $a_{96}$ (t) is the time-varying (because, in general, temperature is changing with time) propellant temperature shift factor. These parameters, along with the exponent B, are measured by performing laboratory tests on tensile coupon samples. Shift factors are derived from relaxation modulus data. The remaining parameters are derived from uniaxial constant rate tensile tests (performed at a number of temperatures and strain rates) and creep testing. $\sigma(t)$ is the input stress history of interest and may be any complex sequences of stresses. The overall load sequence used may be the outcome of the structure's service environment, rather than a specific sequence of stresses. Note that, once the regression coefficients $a_i$ are calculated for use in equation (1), there is no further need to perform a finite element analysis, and no finite element analysis need be performed in the numerical integration of equation (2). Note that in the cumulative damage model, failure is imminent when D reaches unity.

In performing the integration, a Monte Carlo analysis is used, with statistical variation of the inputs to the damage equation (2), as shown in the equations below:

$$E(t) = \overline{E}(t) + s_E d_1 \quad (3)$$

$$T(t) = \overline{T}(t) + s_T(l) d_2 \quad (4)$$

$$\sigma_0(t) = \overline{\sigma}_0(t) + s_{\sigma_0} d_3 \quad (5)$$

$$B(t) = \overline{B}(t) + s_B d_4 \quad (6)$$

where $d_i$ are the random deviates and s is the standard deviation.

Figure 4A:
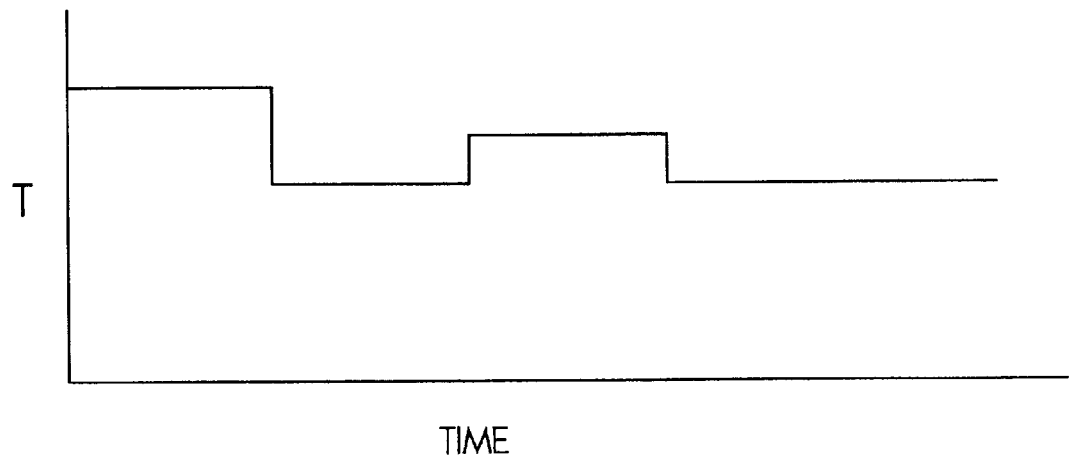
FIGS. 4(a) and (b) are exemplary illustrations of load history step functions.
Figure 4B:
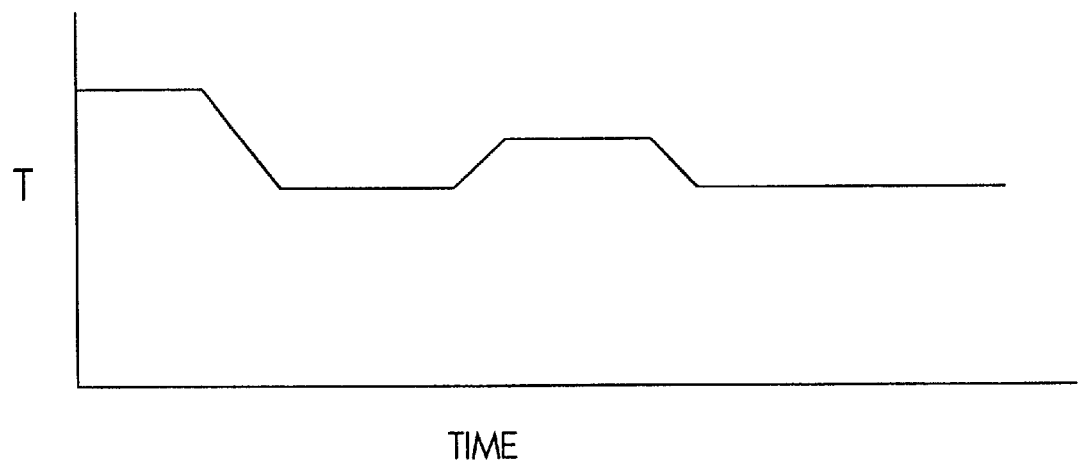

To perform the numerical integration, the load history is first established. For example, this may be a time-temperature history. Generally, this will be expressed as a step function with vertical transitions, as shown in exemplary form in FIG. 4(a). However, especially in the case of thermally induced stress load, where load change is not instantaneous, a trapezoidal step function, as shown in FIG. 4(b), may be used.

Relaxation modulus is calculated for each interval in the step function, thereby creating a modulus history. Equation (1) is then used to create a stress history. The stress history is then inserted into equation (2) to create a damage history.

The numerical integration will generally be performed in conjunction with a Monte Carlo simulation. In performing the Monte Carlo simulation, the values of the parameters used in equations (1) and (2) may be randomly selected to represent the normal statistical variability of the parameters. Examples of these parameters include the modulus E, temperature, T, stress to cause failure in unit time, $\sigma_o$, and the exponent, B, as shown in equations (3) to (6). To determine the normal distribution, generally, mean values and standard deviations are used, and the values of these may be obtained from a variety of sources.

For example, the temperature used in one Monte Carlo iteration load history interval is calculated from the mean temperature and the standard deviation associated with that interval. For example, this may represent variation in temperature around the mean temperature at a storage facility. This may be experimentally determined or estimated. The standard deviation used in the separate intervals will probably be different.

Likewise, the Monte Carlo value for the time-dependent modulus, E(t), is determined from a mean value, $\overline{E}(t)$, and a standard deviation, where $S_E$ is determined from the experimentally determined variability of mechanical properties.

The stress to cause failure in unit time, $\sigma_0$, is likewise varied in each iteration. The mean value, $\overline{\sigma}0(t)$, is the value of this property as a function of age. The standard deviation is derived from a regression fit of the aging function. This is generally based on experimental mechanical property data. B(t) is likewise determined from mechanical property data. As an alternative to the use of a normal distribution in the Monte Carlo simulation, a truncated normal distribution may be used to accommodate the situation where the actual value of a parameter cannot be less than or greater than a certain value.

In the Monte Carlo method, the calculation of D for a load history is repeated for a number of iterations, and the value of D>1 is taken as failure of the structure of interest. The estimated probability of failure is the ratio of the number of iterations in which failure occurs to the total number of iterations.

The following Examples are illustrative of the use of the method of the present invention, but the present invention is not limited to these Examples.

EXAMPLE 1

A computer program named AGEMOD.C has been written to perform the above statistical cumulative damage model method. The computer code is included in the Appendix. The program computes the damage function as a function of time using the most likely values of the input parameters. A sensitivity analysis is then performed by using a Monte Carlo simulation to vary the computed value of various input parameters. AGEMOD has been run on a personal workstation computer.

A sample AGEMOD input file is shown in FIG. 2. Arranged in input data blocks it contains all of the necessary load history, material properties, statistical constants and base finite element results necessary to perform the analysis. In this example the model was used to estimate the probability of solid propellant structural failure in a large population of rocket motors. The first block, labeled (a) on FIG. 2(a), consisting of twenty three lines, is the load environment, in the form of a temperature versus time history. A linear interpolation is made at the transition from one temperature to the next, using the interval of time needed for the motor to reach thermal equilibrium. Using Eqn. (1), AGEMOD computes the corresponding stress. The first column is the time, in days, dwelt at its corresponding temperature, in degrees Celsius, in column two. The third column is the temperatures standard deviation. The fourth column is the daily variation of the mean temperature, not used in this example.

The next data block, (b) in FIG. 2(a), is the variation of stress free temperature with time. In this case the propellant is always under some level of load because it is stress free only slightly above the elevated temperature used to cure it during manufacture. Therefore there are no times when the advance of permanent set stops and the continuous function provided can be used. In general the rate of permanent set accumulation is a function of the specific storage temperatures but for simplicity this has been ignored. The set rate used corresponds to ambient temperature only, which dominates in terms of total dwell time, in the input history.

In general, polymeric materials are classified as being visco-elastic. Their Young's modulus is therefore a function of loading time and temperature. The latter dependence is quantified in the next two blocks (c) and (d) of FIG. 2(a), of input, the respective logarithm (base 10) of the temperature shift factors ($a_\tau$), versus temperature (first column), for the bulk and interface propellant. The two blocks following these (e) of FIG. 2(a) and (f) of FIG. 2(b) are the corresponding logarithm (base 10) of the relaxation modulus (second column) versus logarithm (base 10) of reduced time. These are the respective modulus $E_1$ and $E_2$ in Eqn. 1. Reduced time is the ratio of loading time to temperature shift factor ($t/a_\tau$). AGEMOD uses it to determine values of $E_1$ and $E_2$ for each step in (a) of FIG. 2(a).

The next block, (g), is a modeling parameter, K, (the second column of data). In this example the interface region is a relatively compact zone, about 0.1 inch thick. This is also about the smallest practical size of a tensile test coupon and as such test data of this interface zone actually represent a gradient average. The propellant finite element model is broken into ten 0.01-inch thick elements in this region, each having a different relaxation modulus representing the actual gradient. Since the first 0.01-inch thick propellant element is where structural failure starts it is the modeling region of interest. The parameter $k_t$ is the ratio between the maximum corrected stress expected in the first element and the mean value measured directly from the laboratory tensile coupon. It is found by performing a curve fitting operation involving bulk and interface mean relaxation modulus, interface mean strength and elongation, and fine scale penetrometer profile data. It is used to adjust the laboratory measured values of $\sigma_0$ and $\sigma\infty$ to their corresponding values at d=0.005 inch (the mid point of the first finite element). Since it is possible that $k_t$ might change as the propellant ages, the propellant age at each determination is included (the first column of entries in (g) of FIG. 2(b)). AGEMOD performs a linear regression fit and adjusts $k_t$ accordingly when performing an analysis. The program forces it to assume a constant value once the oldest sample determination is reached. In this case that appeared to be a more realistic approach than continuing to extrapolate the regression line beyond the data. The last column is a list of weighting factors. Each $k_t$ entry is an averaged value computed from data representing a large number of tensile coupons taken from a single propellant sample. The weighting factor can be used to favor determinations based on a larger number of test coupons (in practice it is simply equal to the number of coupons that were tested). Clearly, $k_t$ is very specific to this example but its discussion serves to illustrate the methodology that can be used to analyze anisotropic materials.

The next block, (h), is the finite element reference set. These are used by AGEMOD to perform a regression analysis to determine that $a_i$. The first column is the interface relaxation modulus, $E_2$, the second column the bulk relaxation modulus, $E_1$, and the final column the stress computed from the finite element model. In this instance it was found that the $E_2$ measured directly from the laboratory coupons was sufficient to derive a satisfactory correlation, i.e. it was not necessary to estimate the modulus in the first propellant finite element.

The next block, (i) is the logarithm (base 10) of interface modulus (second column) versus propellant age data that AGEMOD uses to compute $E_{n2}$, as a function of time. A linear regression is used to estimate the relationship. A number of statistical parameters, physical properties and constants are provided in (j). The first line contains the ratio, 0.98, of the population mean Young's modulus, of bulk propellant, to that used in the base model input set. This is a conversion made to shift the problem to one of a generic analysis of the entire population. The adjacent value, 0.130, is the population (lot to lot) standard deviation. Bulk propellant Young's modulus is treated this way (rather than including the individual values) because its data base is large and couldn't be explicitly included in the AGEMOD input file in a convenient way. If the analysis were being performed for a specific production lot, the ratio reflecting its Young's modulus would be used and the standard deviation would be set to zero since there would be, by definition, no lot-to-lot variability to contend with.

The next line is the maximum expected value of $E_{n1}$. The adjacent entry is the time needed to approach half of this value. This parameter appeared to follow an asymptotic curve and this is what AGEMOD uses to fit the parameter with. The next line contains the corresponding within lot standard deviation values of the logarithm (base 10) of the bulk and interface temperature shift factor. The line after that contains the logarithm (base 10) of the respective values of bulk and interface relaxation modulus within lot standard deviations. The next lines contain the input values of K, $\sigma\infty$, and $t_o$ (here expressed as one minute in units of days since the $t/a_T$ data were expressed in minutes). It should be noted that the aging function models governing bulk and interface propellant are not the same. They were selected to provide the optimum fit of the raw data sets and illustrate the flexibility available within AGEMOD.

The next block of data (k) are the values of the logarithm (base 10) of $\sigma_0$ (second column) versus propellant age. AGEMOD accounts for changes in this parameter by performing a linear regression analysis of these data. There is also a weighting factor because each $\sigma_0$ is computed from a number of test samples. The final data block (l) contains the values of the exponent B (second column) versus propellant age. These data are treated in the same was as is $\sigma_0$ except that the standard deviation can be specified.

The final line of input contains the number of statistical, or Monte Carlo, iterations AGEMOD is to perform. In a given iteration AGEMOD perturbs the mean value of each parameter in Eqn. (2) by a randomly determined deviate combined with the parameters standard deviation (either directly input or computed internally). A different deviate is used for each temperature in the sequence (a). Variables that are physically coupled are perturbed by a common deviate, e.g. $E_2$ and $\sigma_0$ were linked to avoid the unrealistic combination of a high modulus and a low stress or vice versa.

The resulting total cumulative damage from each iteration is tabulated. At each step in the input load history AGEMOD computes a structure reliability defined as the number of iterations where the total damage, to that point, is less than unity divided by the total number of iterations made. The initial integer seed provides a reference point from which the stream of random deviates starts, i.e. using the same seed for successive analysis results in the same set of random deviates being used for each. This may be useful when making comparative runs in which some of the input variables are being changed.

We have found that when a large number of iterations are specified a more precise reliability estimate is obtained. This is, of course, at the expense of a longer run time. In general a system with a fairly high reliability will require more iterations to estimate reliability than a less reliable structure will, e.g. if 1,000 iterations are run and the estimated reliability is 1.0 (no instances of D>1 are encountered) little has been revealed about the true failure rate. A run consisting of 10,000 iterations on a thirty step load history can be run in less than twenty minutes on a conventional work station. The key is that Eqn. 1 is used to estimate the stresses rather than using a more time-consuming finite element model.

EXAMPLE 2

Figure 3:
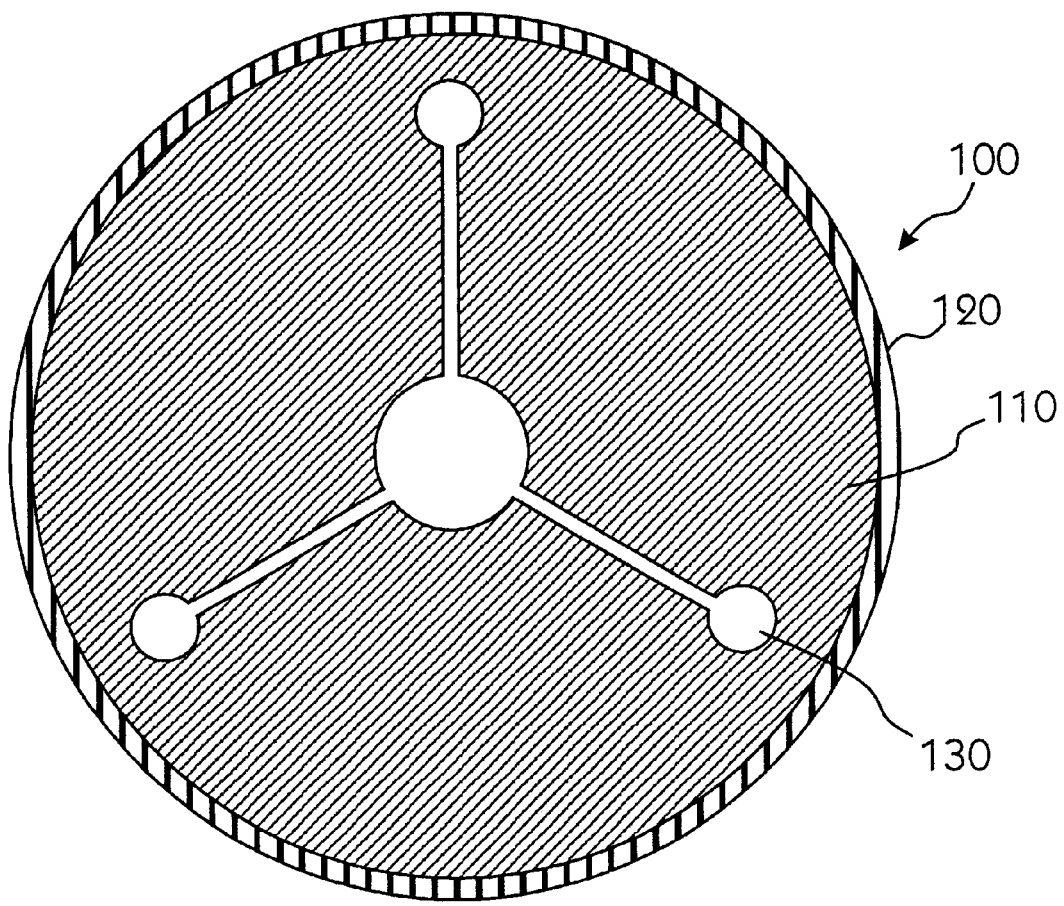
FIG. 3 is a cross-sectional diagram of a rocket motor whose failure may be modeled using the present invention.

Example 2 illustrates the use of the method of the present invention to model failure of the an exemplary solid propellant rocket motor 100, shown in cross-section in FIG. 3. Solid propellant 110 may be constructed with a highly filled polymer bonded to the steel case 120 of the motor. A thin layer of rubber is bonded to all internal surfaces. The peak stress area occurs in the bulk tip 130 of the propellant.

Bulk propellant properties were determined by laboratory testing of specimens taken from the solid propellant 110. These included stress-free temperature shift. The mechanical properties of interface propellant were determined using 2.5-mm thick mini-dogbone samples, taken from the internal surface that contains the bulk tip 130. Chemical interaction of the propellant with a rubber liner (not shown) creates a non-homogeneity in the propellant there.

The Monte Carlo simulation was performed by varying each of the parameters in equations (1) and (2) within the respective estimated normal distribution, as shown in equations (3) to (6). This is repeated a number of times for the given load sequence, and the fraction of times in which failure is calculated to occur, that is, in which D>1.0, is determined, thereby giving the predicted probability of failure. The Monte Carlo simulation in this case was performed using the computer program AGEMOD, discussed in Example 1.

A simulation was performed of a nineteen-day thermal cycling (five days at each of 130° F. and −20° F. followed by three cycles of thirty-six dwells at each of 130° F. and −20° F.) for newly manufactured motors. Each motor's known bulk grain Young's modulus was used in the model.

In a lot of 50 motors with Young's moduli ranging from 764 psi to 1433 psi, one failure was observed. This observed failure rate of 0.02 can be used to estimate a 90% confidence interval of failure rate of approximately 0.01 to 0.08. By comparison, failure rates for the motors estimated using the AGEMOD program as described above were dependent on the Young's modulus, and varied from about 0.03 for propellant with a Young's modulus of 764 psi to a rate of approximately 0.11 for propellant with a Young's modulus of 1433 psi. Thus, the estimated failure rate of this lot of motors is consistent with the experimentally observed rate.

The method of the present invention can be seen in the Examples to provide an easily obtained and rapid estimate of the cumulative thermal damage to a filled polymeric propellant of a solid rocket motor, allowing estimation of the time to failure. It must be emphasized that thermal contraction is not the only loading mechanism to which the present invention may be applied. For example, if the mode of loading where the simple extension of a structural member, a length ratio, analogous to the temperature ratio, could be used in equation (1). The same procedure for finding the values of $a_i$ would be employed, the only difference being that they would be computed at a reference length instead of a reference temperature. For example, equation (1) could be expressed in terms of strain.

Likewise, the Examples have illustrated the method of the present invention applied to solid propellant rocket motors. However, the present invention is in principle applicable to many different filled polymeric systems.

The present invention has been described in an illustrative manner, and many modifications and variations are possible in light of the above teachings. It is therefore to be understood that, within the scope of the appended claims, the invention may be practiced other than as specifically described.

PATENT
NAVY CASE No. 78,988

APPENDIX

PATENT
NAVY CASE No. 78,988

AGEMOD.C
```
/* ================================================================ */
/* STATISTICAL CUMULATIVE DAMAGE MODEL FOR STRUCTURAL ANALYSIS OF FILLED
   POLYMERIC MATERIALS                              VERSION 1.0 */
/* ================================================================ */
/* John Jay Nestor III                                              */
/* ---------------------------------------------------------------- */
/* Started: 03/27/96                          Ended: xx/xx/96       */
/* ---------------------------------------------------------------- */
/* This program computes the damage function as a                   */
/* function of time using the most likely values of the input parameters. */
/* A sensitivity analysis is then performed by using a Monte Carlo  */
/* simulation to vary the computed value of various input parameters. */
/* The damage function integration is performed                     */
/* using the Runge-Kutta method with adaptive step size control     */
/* See Numerical Recipes in C, Press, Flannery,                     */
/* Teukolsky and Vetterling, p. 582-586.                            */
/* ================================================================ */

/* ---------------------------------------------------------------- */
/* Remember to include the proper ANSI-standard C function libraries. */
/* ---------------------------------------------------------------- */
#include <stdlib.h>
#include <stdio.h>
#include <ctype.h>
#include <math.h>
#include "nr.h"
#include "nrutil.h"

/* ---------------------------------------------------------------- */
/* define macros for ode integrator parameters                      */
/* TWOPI : twice the mathematical constant pi                       */
/* EPSLON: relative error tolerance for ode integrator              */
/* EPSBRT: absolute error tolerance for root finder                 */
/* TINY  : small positive constant                                  */
/* CONFID: confidence level for upper failure probability           */
/* WLFC1 : initial value for C1 constant in WLF equation            */
/* WLFC2 : initial value for C2 constant in WLF equation            */
/* NVAR  : number of dependent variables (i.e. equations) in system */
/* NWLF  : number of undetermined coefficients in WLF equation      */
/* NLINR : number of undetermined coefficients in linear polynomial */
/* NQUAD : number of undetermined coefficients in quadratic polynomial */
/* NCUBE : number of undetermined coefficients in cubic polynomial  */
/* SQR(a): square of the argument a                                 */
/* ---------------------------------------------------------------- */ define TWOPI 6.28318530717959
define EPSLON 1.0e-06
#define EPSBRT 1.0e-06
#define TINY 1.0e-06
#define CONFID 0.95
#define WLFC1 -9.0
#define WLFC2 100.0
#define NVAR 1
#define NWLF 3
#define NLINR 2
#define NQUAD 3
```

PATENT
NAVY CASE No. 78,988

```c
define NCUBE 4 static float sqrarg;
define SQR(a) (sqrarg=(a),sqrarg*sqrarg)

/* ---------------------------------------------------------------- */
/* Declare global variable keybuffer - this is now going to be the key- */
/* board buffer for sscanf, since I don't like the way scanf will only  */
/* buffer on a carriage return                                          */
/* ---------------------------------------------------------------- */ char keybuffer[79];

/* ---------------------------------------------------------------- */
/* Declare all global variables found in this program               */
/* ---------------------------------------------------------------- */

/* ---------------------------------------------------------------- */
/* idum  : integer seed for random deviate generation               */
/* iterno: current iteration number                                 */
/* ---------------------------------------------------------------- */ int idum,iterno;

/* ---------------------------------------------------------------- */
/* tinitl: initial time for damage computation                      */
/* tfinal: termination time for damage computaion                   */
/* ---------------------------------------------------------------- */ float tinitl,tfinal;

/* ---------------------------------------------------------------- */
/* numpro: number of points in temperature vs time profile          */
/* timpro: array of times at which temperature profile is input     */
/* tmppro: array of temperatures at corresponding values in array timpro */
/* tmpsig: array of standard deviation of temperatures at corresponding  */
/*         values in array timpro                                   */
/* tmpran: gaussian random deviate for temperature at corresponding */
/*         values in array timpro                                   */
/* tmpamp: amplitude of temperature variation                       */
/* tmpfrq: frequency of temperature variation                       */
/* rlxtim: relaxation period between time steps                     */
/* ---------------------------------------------------------------- */ float *timpro,*tmppro,*tmpsig,*tmpran,*tmpamp,tmpfrq,rlxtim;
int numpro;

/* ---------------------------------------------------------------- */
/* Temperature shift factor modeling coefficients                   */
/* numatb: number of points in log10(at(bulk)) vs temp profile      */
/* atbtmp: array of temps at which log10(at(bulk)) profile is given */
/* logatb: array of log10(at(bulk)) parameter values at corr. temp  */
/* numati: number of points in log10(at(intf)) vs temp profile      */
/* atitmp: array of temps at which log10(at(intf)) profile is given */
/* logati: array of log10(at(intf)) parameter values at corr. temp  */
/* trefbk: initial reference temperature for at(bulk)               */
/* trefin: initial reference temperature for at(intf)               */
```

Page 27

PATENT
NAVY CASE No. 78,958

```
/* atbsig: value of standard deviation of log10(at(bulk))        */
/* atisig: value of standard deviation of log10(at(intf))        */
/* atbran: current log normal random deviate for at(bulk)        */
/* atiran: current log normal random deviate for at(intf)        */
/* atbulk: current value of log10(at(bulk))                      */
/* atintf: current value of log10(at(intf))                      */
/* ------------------------------------------------------------- */ float *atbtmp,*logatb,*atitmp,*logati;
int numatb,numati;
float trefbk,trefin;
float atbsig,atisig,atbran,atiran,atbulk,atintf;

/* ------------------------------------------------------------- */
/* Stress free temperature parameters                            */
/* numtsf: number of points in stress free temperature vs time profile */
/* timtsf: array of times at which stress free temperature is input    */
/* tsfpro: array of stress free temperatures at corresponding values in */
/*         timtsf                                                */
/* tsfint: initial stress free temperature                       */
/* tsfamb: ambient shifted stress free temperature               */
/* sfrsig: standard deviation of set fraction                    */
/* sfrran: current normal random deviate for set fraction        */
/* tempfe: temperature of finite element analysis set            */
/* ------------------------------------------------------------- */ float tsfint,tsfamb,sfrsig,sfrran,tempfe;
float *timtsf,*tsfpro;
int numtsf;

/* ------------------------------------------------------------- */
/* Relaxation modulus parameters                                 */
/* numebk: number of points in log10 e(bulk) vs log10(time/at) profile */
/* ebktat: array of log10(time/at) values in log10 e(bulk) profile     */
/* logebk: array of log10 e(bulk) modulus values in profile      */
/* numein: number of points in log10 e(intf) vs log10(time/at) profile */
/* eintat: array of log10(time/at) values in log10 e(intf) profile     */
/* logein: array of log10 e(intf) modulus values in profile      */
/* timint: current value of relaxation modulus time interval     */
/* ebulk : current value of bulk relaxation modulus              */
/* ebrati: current value of ratio between bulk relaxation modulus */
/*         and Class B relaxation modulus                        */
/* ebrtmu: mean value of ebrati                                  */
/* ebrtsg: standard deviation of ebrati (normal distribution)    */
/* eintf : current value of interface relaxation modulus         */
/* ebksig: standard deviation of log10 (ebulk)                   */
/* einsig: standard deviation of log10 (eintf)                   */
/* ebkran: current log normal random deviate for ebulk           */
/* einran: current log normal random deviate for eintf           */
/* ------------------------------------------------------------- */ float *ebktat,*logebk,*eintat,*logein;
int numebk,numein;
float timint,ebulk,ebrati,ebrtmu,ebrtsg;
float eintf,ebksig,einsig,ebkran,einran;

/* ------------------------------------------------------------- */
```

PATENT
NAVY CASE No. 78,988

```
/* Stress model parameters                                                    */
/* numkt : number of points in kt vs age profile                              */
/* ktage : array of ages at which kt parameter data is input                  */
/* ktpro : array of kt parameter values at corresponding ages in ktage        */
/* ktwgt : array of statistical weights to apply to kt parameter data         */
/* ktsig : standard deviation of log (base 10) of kt                          */
/* ktran : current random deviate for kt parameter                            */
/* enmax : maximum ratio between aged and unaged bulk modulus                 */
/* enlmb : mean time for aged bulk modulus to increase 50% of the             */
/*         difference between current ebulk and enmax                         */
/* numem : number of points in em profile                                     */
/* emage : array of ages at which interface modulus is input for aging        */
/*         trend                                                              */
/* empro : array of log (base 10) of interface modulus at corresponding       */
/*         ages in emage                                                      */
/* numstr: number of points in stress regression analysis profile             */
/* ebspro: array of bulk modulus values for stress regression analysis        */
/* eispro: array of interface modulus values for stress regression            */
/* sigpro: array of corrected stress values at corresponding values           */
/*         of bulk and interface modulus values                               */
/* k3d    : three dimensional concentration factor                            */
/* -------------------------------------------------------------------------- */ int numkt,numem,numstr;
float *ktage,*ktpro,*ktwgt,ktsig,ktran;
float enmax,enlmb,*emage,*empro;
float *ebspro,*eispro,*sigpro,k3d;

/* -------------------------------------------------------------------------- */
/* Damage function parameters                                                 */
/* strthr: mean minimum threshold corrected stress for damage occurrence      */
/* tau0  : time scale unit for time to failure curves                         */
/* numsg0: number of points in log10(sigma0) vs age profile                   */
/* sg0age: array of ages at which log10(sigma0) is input                      */
/* sg0pro: array of log10(stress) required to produce failure in time         */
/*         tau0 at corresponding ages in profile                              */
/* sg0wgt: array of statistical weights to apply to sigma0 data               */
/* numstb: number of points in stb vs age profile                             */
/* stbage: array of ages at which stb parameter is input                      */
/* stbpro: array of negative reciprocals of slope of log corrected            */
/*         stress vs log (base 10) reduced time to failure curve              */
/* stbwgt: array of statistical weights to apply to stb data                  */
/* stbsig: standard deviation of stb parameter                                */
/* stbran: stb parameter random deviate                                       */
/* -------------------------------------------------------------------------- */ int numsg0,numstb;
float strthr,tau0,*sg0age,*sg0pro,*sg0wgt,*stbage,*stbpro,*stbwgt;
float stbsig,stbran;

/* -------------------------------------------------------------------------- */
/* Statistical output parameters                                              */
/* numitr: number of Monte Carlo iterations                                   */
/* strpro: array of most likely stress values computed at array of times      */
/*         input as part of temperature profile                               */
/* tsftmp: array of most likely stress free temperatures computed at          */
/*         times input as part of temperature profile                         */
```

PATENT
NAVY CASE No. 78,988

```
/* ebkpro: array of most likely bulk modulus values computed          */
/*         times input as part of temperature profile                 */
/* einpro: array of most likely interface modulus values computed at  */
/*         times input as part of temperature profile                 */
/* dampro: array of most likely log10(damage fractions) accumulated   */
/*         at array of times input as part of temperature profile     */
/* lsfpro: array of factors which when multiplied by computed stress  */
/*         values at all times produces a damage factor of 1.0        */
/*         at input temperature profile times                         */
/* rellim: array of one-sided lower confidence limit reliability      */
/*         probabilities of damage NOT exceeding 1.0                  */
/* nfail : array of number of Monte Carlo iterations in which         */
/*         accumulated damage fractions exceed 1.0 at specified       */
/*         temperature profile times                                  */
/* corran: correlated random deviate draw                             */
/* betap : current value of beta density p parameter (num failures + 1) */
/* betaq : current value of beta density q parameter (num successes + 1) */
/* damsim: array of common logarithm of accumulated damage fractions at */
/*         temperature profile times                                  */
/* ------------------------------------------------------------------ */ int numitr;
float *strpro,*tsftmp,*ebkpro,*einpro, *dampro,*lsfpro,*rellim;
float corran,betap,betaq;
int *nfail;
float **damsim;

/* ------------------------------------------------------------------ */
/* I/O files                                                          */
/* infile: array containing input filename                            */
/* outfil: array containing output filename                           */
/* simout: array containing simulation output filename                */
/* ------------------------------------------------------------------ */ char infile[80],outfil[80],simout[80];

/* ------------------------------------------------------------------ */
/* Prototype all functions found in this program                      */
/* ------------------------------------------------------------------ */

/* ------------------------------------------------------------------ */
/* Define function fpolyn                                             */
/* Use: define a set of basis functions for a polynomial fit          */
/* Pre: the function is passed the independent variable x and the order */
/*      of the fit polynomial                                         */
/* Act: the function computes the value of the polynomial basis       */
/*      functions at x                                                */
/* Pst: the function returns the value of the basis functions evaluated */
/*      at x                                                          */
/* ------------------------------------------------------------------ */
void fpolyn (x,afunc,mma)
float x,*afunc;
int mma;
{
    int i;

afunc[1] = 1.0e0;
```

```
    for (i=2;i<=mma;i++) afunc[i] = x*afunc[i-1];
}

/* ---------------------------------------------------------------- */
/*                                                                  */
/* Define function temper                                           */
/* Use: the function computes the temperature at the given time     */
/* Pre: the function is passed the value of the time parameter      */
/* Act: the function uses the temperature at the nearest previous   */
/*      time step unless the time is within rlxtim of the next time step */
/*      in which case it uses a linearly interpolated value         */
/* Pst: the function returns the interpolated value at the requested time*/
/* ---------------------------------------------------------------- */
float temper (ttime)
float ttime;
{
    static int j=0;
    int i;
    float *xa,*ya,y,dy;

hunt (timpro,numpro,ttime,&j);

if (j <= 0)
    {
        return(tmpran[1] +
               tmpamp[1]*cos((double)(TWOPI*tmpfrq*ttime)));
    }
    if (j >= numpro)
    {
        return(tmpran[numpro] +
               tmpamp[numpro]*cos((double)(TWOPI*tmpfrq*ttime)));
    } if ((timpro[j+1] - rlxtim) > ttime)
    {
        y = tmpran[j];
    }
    else
    {
        xa = vector(1,2);
        ya = vector(1,2);

if ((timpro[j+1] - rlxtim) > timpro[j])
            xa[1] = timpro[j+1] - rlxtim;
        else
            xa[1] = timpro[j];
        ya[1] = tmpran[j];
        xa[2] = timpro[j+1];
        ya[2] = tmpran[j+1];

polint(xa,ya,NLINR,ttime,&y,&dy);

free_vector (xa,1,2);
        free_vector (ya,1,2);
    } return (y + tmpamp[j]*cos((double)(TWOPI*tmpfrq*ttime)));
```

PATENT
NAVY CASE No. 78,988

}

```c
/* ---------------------------------------------------------------- */
/* Define function wlfeqn                                           */
/* Use: the function computes the log10(at) and its derivatives     */
/*      according to the WLF formula                                */
/* Pre: the function is passed the temperature and fitting parameters */
/* Act: the function computes the log10(at) and its derivatives with */
/*      respect to the fitting parameters                           */
/* Pst: the function returns the values of the log10(at) and its    */
/*      derivatives at the prescribed temperature in the appropriate */
/*      arrays                                                      */
/* ---------------------------------------------------------------- */
void wlfeqn (ttemp,param,y,dy,nparam)
float ttemp,param[],*y,dy[];
int nparam;
{
     float denom,temp1,densq;

temp1 = ttemp - param[3];
     denom = param[2] + temp1;
     densq = SQR(denom);

*y    = param[1]*temp1/denom;
     dy[1] = temp1/denom;
     dy[2] = -(*y)/denom;
     dy[3] = -param[1]*param[2]/densq;

/* ---------------------------------------------------------------- */
/* Define function atblog                                           */
/* Use: the function computes the temperature shift factor, log10(atb) */
/* Pre: the function is passed the value of the temperature         */
/* Act: the function computes the temperature shift factor for the  */
/*      bulk modulus by fitting a wlf model to the input data       */
/*      and then applying the model for the input temperature       */
/* Pst: the function returns the log(base 10) of the temperature shift */
/*      factor                                                      */
/* ---------------------------------------------------------------- */
float atblog (ttemp)
float ttemp;
{
     static int iff=0;
     static float *sig,*atbcof,**covar,**alpha,
                  alamda,chisq,ochisq;
     float *init;
     float value,*dydt;
     int i,itst,mfit,*lista;

if (iff == 0)
     {
          iff = 1;
          lista = ivector(1,NWLF);
          sig = vector(1,numatb);
          init = vector(1,NWLF);
```

PATENT
NAVY CASE No. 78,988

```
        atbcof = vector(1,NWLF);
        covar = matrix (1,NWLF,1,NWLF);
        alpha = matrix (1,NWLF,1,NWLF);
        init[1] = WLFC1;
        init[2] = WLFC2;
        init[3] = trefbk;

for (i=1;i<=numatb;i++)
        {
              sig[i] = 1.0e0;
        } mfit = NWLF;
        for (i=1;i<=NWLF;i++)
        {
              lista[i] = i;
              atbcof[i] = init[i];
        }
        alamda = -1;

mrqmin(atbtmp,logatb,sig,numatb,atbcof,NWLF,lista,mfit,covar,
              alpha,&chisq,wlfeqn,&alamda);

itst = 0;

while (itst < 2)
        {
              ochisq = chisq;
              mrqmin(atbtmp,logatb,sig,numatb,atbcof,NWLF,lista,mfit,
                    covar,alpha,&chisq,wlfeqn,&alamda);
              if (chisq > ochisq)
                    itst = 0;
              else if (fabs(ochisq-chisq) < 0.1)
                    itst++;
        } alamda=0.0e0;
        mrqmin(atbtmp,logatb,sig,numatb,atbcof,NWLF,lista,mfit,covar,
              alpha,&chisq,wlfeqn,&alamda);

free_matrix(alpha,1,NWLF,1,NWLF);
        free_matrix(covar,1,NWLF,1,NWLF);
        free_vector(sig,1,numatb);
        free_ivector(lista,1,NWLF);

} dydt = vector(1,NWLF);
    wlfeqn (ttemp,atbcof,&value,dydt,NWLF);
    free_vector(dydt,1,NWLF);

return (value + atbran);
}
/* ---------------------------------------------------------------- */
/* Define function atilog                                           */
/* Use: the function computes the temperature shift factor, log10(ati) */
```

```
                                                                              PATENT
                                                                    NAVY CASE No. 78,988

/* Pre: the function is passed the value of the temperature              */
/* Act: the function computes the temperature shift factor for the       */
/*      bulk modulus by fitting a wlf model to the input data            */
/*      and then applying the model for the input temperature            */
/* Pst: the function returns the log(base 10) of the temperature shift   */
/*      factor                                                           */
/* --------------------------------------------------------------------- */
float atilog (ttemp)
float ttemp;
{
     static int iff=0;
     static float *sig,*aticof,**covar,**alpha,
                  alamda,chisq,ochisq;
     float *init;
     float value,*dydt;
     int i,itst,mfit,*lista;

if (iff == 0)
     {
         iff = 1;
         lista = ivector(1,NWLF);
         sig = vector(1,numati);
         init = vector(1,NWLF);
         aticof = vector(1,NWLF);
         covar = matrix (1,NWLF,1,NWLF);
         alpha = matrix (1,NWLF,1,NWLF);
         init[1] = WLFC1;
         init[2] = WLFC2;
         init[3] = trefin;

for (i=1;i<=numati;i++)
         {
              sig[i] = 1.0e0;
         } mfit = NWLF;
         for (i=1;i<=NWLF;i++)
         {
              lista[i] = i;
              aticof[i] = init[i];
         }
         alamda = -1;

mrqmin(atitmp,logati,sig,numati,aticof,NWLF,lista,mfit,covar,
                alpha,&chisq,wlfeqn,&alamda);

itst = 0;

while (itst < 2)
         {
              ochisq = chisq;
              mrqmin(atitmp,logati,sig,numati,aticof,NWLF,lista,mfit,
                     covar,alpha,&chisq,wlfeqn,&alamda);
              if (chisq > ochisq)
                  itst = 0;
              else if (fabs(ochisq-chisq) < 0.1)
                  itst++;
```

PATENT
NAVY CASE No. 78,988

```
        } alamda=0.0e0;
        mrqmin(atitmp,logati,sig,numatb,aticof,NWLF,lista,mfit,covar,
                alpha,&chisq,wlfeqn,&alamda);

free_matrix(alpha,1,NWLF,1,NWLF);
        free_matrix(covar,1,NWLF,1,NWLF);
        free_vector(sig,1,numati);
        free_ivector(lista,1,NWLF);

} dydt = vector(1,NWLF);
    wlfeqn (ttemp,aticof,&value,dydt,NWLF);
    free_vector(dydt,1,NWLF);

return (value + atiran);
}

/* ------------------------------------------------------------ */
/*                                                              */
/* Define function ebklog                                       */
/* Use: the function computes the bulk relaxation modulus, log10(ebk) */
/* Pre: the function is passed the value of the log10(time/at)  */
/* Act: the function computes the log base 10 of the            */
/*      bulk modulus by fitting a cubic model to the input data */
/*      and then applying the model for the input value of log10(time/at)*/
/* Pst: the function returns the log(base 10) of the bulk relaxation */
/*      modulus                                                 */
/* ------------------------------------------------------------ */
float ebklog (logtat)
float logtat;
{
    static int iff=0;
    static float *sig,*ebkcof,**u,**v,*w,**cvm,chisq;
    float value,*afunc;
    int i;

if (iff == 0)
    {
        iff = 1;
        sig = vector(1,numebk);
        ebkcof = vector(1,NCUBE);
        u = matrix(1,numebk,1,NCUBE);
        v = matrix(1,NCUBE,1,NCUBE);
        w = vector(1,NCUBE);
        cvm = matrix(1,NCUBE,1,NCUBE);

for (i=1;i<=numebk;i++) sig[i] = 1.0e0;

svdfit(ebktat,logebk,sig,numebk,ebkcof,NCUBE,u,v,w,&chisq,fpolyn);
        svdvar(v,NCUBE,w,cvm);

free_matrix(u,1,numebk,1,NCUBE);
        free_matrix(v,1,NCUBE,1,NCUBE);
        free_vector(w,1,NCUBE);
        free_matrix(cvm,1,NCUBE,1,NCUBE);
```

Page 35

PATENT
NAVY CASE No. 78,988

```
      free_vector(sig,1,numebk);
   } afunc = vector(1,NCUBE);
   fpolyn (logtat,afunc,NCUBE);

value = 0.0e0;
   for (i=1;i<=NCUBE;i++) value += ebkcof[i]*afunc[i];

free_vector(afunc,1,NCUBE);

return (value + ebkran + logten(ebrati));
}
/* ---------------------------------------------------------------- */
/*                                                                  */
/* Define function einlog                                           */
/* Use: the function computes the interface relaxation modulus,log10(ein)*/
/* Pre: the function is passed the value of the log10(time/at)      */
/* Act: the function computes the log base 10 of the interface      */
/*      modulus by fitting a cubic model to the input data and then */
/*      applying the model for the input value of log10(time/at)    */
/* Pst: the function returns the log(base 10) of the interface relaxation*/
/*      modulus                                                     */
/* ---------------------------------------------------------------- */
float einlog (logtat)
float logtat;
{
   static int ifg=0;
   static float *sig,*eincof,**u,**v,*w,**cvm,chisq;
   float value,*afunc;
   int i;

if (ifg == 0)
   {
      ifg = 1;
      sig = vector(1,numein);
      eincof = vector(1,NCUBE);
      u = matrix(1,numein,1,NCUBE);
      v = matrix(1,NCUBE,1,NCUBE);
      w = vector(1,NCUBE);
      cvm = matrix(1,NCUBE,1,NCUBE);

for (i=1;i<=numein;i++) sig[i] = 1.0e0;

svdfit(eintat,logein,sig,numein,eincof,NCUBE,u,v,w,&chisq,fpolyn);
      svdvar(v,NCUBE,w,cvm);

free_matrix(u,1,numein,1,NCUBE);
      free_matrix(v,1,NCUBE,1,NCUBE);
      free_vector(w,1,NCUBE);
      free_matrix(cvm,1,NCUBE,1,NCUBE);
      free_vector(sig,1,numein);
   } afunc = vector(1,NCUBE);
   fpolyn (logtat,afunc,NCUBE);
```

```
    value = 0.0e0;
    for (i=1;i<=NCUBE;i++) value += eincof[i]*afunc[i];

free_vector(afunc,1,NCUBE);

return (value + einran);
}
/* ---------------------------------------------------------------- */
/*                                                                  */
/* Define function blkage                                           */
/* Use: the function computes the ratio of aged/unaged bulk modulus */
/*      values                                                      */
/* Pre: the function is passed the current age, maximum ratio and mean */
/*      time for modulus to increase 50% of the difference between its */
/*      current and maximum value                                   */
/* Act: the function computes the current ratio using an exponential */
/*      decay model                                                 */
/* Pst: the function returns the current value of the ratio         */
/* ---------------------------------------------------------------- */
float blkage (tage, maxrat, lambda)
float tage,maxrat,lambda;
{
    float decay;

decay = exptwo(-tage/lambda);
    return (maxrat - decay*(maxrat - 1.0e0));
}

/* ---------------------------------------------------------------- */
/*                                                                  */
/* Define function intage                                           */
/* Use: the function computes the ratio of aged/unaged bulk modulus */
/*      values                                                      */
/* Pre: the function is passed the current age                      */
/* Act: on the first call, the function computes the linear regression */
/*      coefficient of log (base 10) of interface modulus versus age; */
/*      on all subsequent calls, the function uses the computed     */
/*      regression coefficient to calculate the desired ratio       */
/* Pst: the function returns the current value of the ratio         */
/* ---------------------------------------------------------------- */
float intage (tage)
float tage;
{
    static int ifd=0;
    static float *sig,*intcof,**u,**v,*w,**cvm,chisq;
    float time,value,*afunc;
    int i;

if (ifd == 0)
    {
        ifd = 1;
        sig = vector(1,numem);
        intcof = vector(1,NLINR);
        u = matrix(1,numem,1,NLINR);
        v = matrix(1,NLINR,1,NLINR);
        w = vector(1,NLINR);
        cvm = matrix(1,NLINR,1,NLINR);
```

PATENT
NAVY CASE No. 78,988

```
    for (i=1;i<=numem;i++) sig[i] = 1.0e0;

svdfit(emage,empro,sig,numem,intcof,NLINR,u,v,w,&chisq,fpolyn);
    svdvar(v,NLINR,w,cvm);

free_matrix(u,1,numem,1,NLINR);
    free_matrix(v,1,NLINR,1,NLINR);
    free_vector(w,1,NLINR);
    free_matrix(cvm,1,NLINR,1,NLINR);
    free_vector(sig,1,numem);
} if (tage <= emage[numem])
{
    time = tage;
}
else
{
    time = emage[numem];
} afunc = vector(1,NLINR);
fpolyn (time,afunc,NLINR);

value = 0.0e0;
for (i=2;i<=NLINR;i++) value += intcof[i]*afunc[i];

free_vector(afunc,1,NLINR);

return (expten(value));

/* -------------------------------------------------------------- */
/*                                                                */
/* Define function tempsf                                         */
/* Use: the function computes the shifted stress free temperature */
/* Pre: the function is passed the time since manufacture         */
/* Act: the function computes the current stress free temperature by */
/*      using linear interpolation of the input table and adding  */
/*      the random component due to variation in the set fraction */
/* Pst: the function returns the current value of the stress free */
/*      temperature                                               */
/* -------------------------------------------------------------- */
float tempsf (tage)
float tage;
{
    static int k=0;
    int i;
    float *xa,*ya,y,dy;

hunt (timtsf,numtsf,tage,&k);

if (k <= 0)
    {
        return (tsfpro[1] + (tsfamb - tsfint)*sfrran);
    }
    if (k >= numtsf)
    {
```

Page 38

```
    return (tsfpro[numtsf] + (tsfamb - tsfint)*sfrran);
} xa = vector(1,2);
ya = vector(1,2);

xa[1] = timtsf[k];
ya[1] = tsfpro[k];
xa[2] = timtsf[k+1];
ya[2] = tsfpro[k+1];

polint(xa,ya,NLINR,tage,&y,&dy);

free_vector (xa,1,2);
free_vector (ya,1,2);

return (y + (tsfamb - tsfint)*sfrran);

}
/* ------------------------------------------------------------ */
/*                                                              */
/* Define function ktfunc                                       */
/* Use: the function computes the value of the kt parameter     */
/* Pre: the function is passed the current age                  */
/* Act: the function computes the value of the kt parameter as a function */
/*      of age by fitting a partial linear regression to the input data */
/* Pst: the function returns the computed value of kt           */
/* ------------------------------------------------------------ */
float ktfunc (tage)
float tage;
{
    static int ife=0;
    static float *sig,*ktcof,**u,**v,*w,**cvm,chisq;
    float time,value,*afunc;
    int i;

if (ife == 0)
    {
        ife = 1;
        sig = vector(1,numkt);
        ktcof = vector(1,NLINR);
        u = matrix(1,numkt,1,NLINR);
        v = matrix(1,NLINR,1,NLINR);
        w = vector(1,NLINR);
        cvm = matrix(1,NLINR,1,NLINR);

for (i=1;i<=numkt;i++) sig[i] = 1.0/sqroot(ktwgt[i]);

svdfit(ktage,ktpro,sig,numkt,ktcof,NLINR,u,v,w,&chisq,fpolyn);
        svdvar(v,NLINR,w,cvm);

free_matrix(u,1,numkt,1,NLINR);
        free_matrix(v,1,NLINR,1,NLINR);
        free_vector(w,1,NLINR);
        free_matrix(cvm,1,NLINR,1,NLINR);
        free_vector(sig,1,numkt);
    }
```

PATENT
NAVY CASE No. 78,988

```
    if (tage <= ktage[numkt])
    {
        time = tage;
    }
    else
    {
        time = ktage[numkt];
    } afunc = vector(1,NLINR);
    fpolyn (time,afunc,NLINR);

value = 0.0e0;
    for (i=1;i<=NLINR;i++) value += ktcof[i]*afunc[i];

free_vector(afunc,1,NLINR);

return (expten(logten(value) + ktran));
}

/* ---------------------------------------------------------------- */
/*                                                                  */
/* Define function sigmai                                           */
/* Use: the function computes the minimum corrected                 */
/*      stress necessary to cause failure                           */
/* Pre: the function is passed the current age                      */
/* Act: the function computes the mean of the minimum               */
/*      corrected stress necessary to cause failure                 */
/* Pst: the function returns the computed value of sigmai           */
/* ---------------------------------------------------------------- */
float sigmai (tage)
float tage;
{
    return (ktfunc(tage)*strthr);
}

/* ---------------------------------------------------------------- */
/*                                                                  */
/* Define function sigma0                                           */
/* Use: the function computes the corrected                         */
/*      stress necessary to cause failure in time tau0              */
/* Pre: the function is passed the current age                      */
/* Act: the function computes the mean of the log (base 10) of the  */
/*      corrected stress necessary to cause failure in time tau0    */
/*      using a linear regression analysis fit                      */
/* Pst: the function returns the computed value of sigma0           */
/* ---------------------------------------------------------------- */
float sigma0 (tage)
float tage;
{
    static int ifa=0;
    static float *sig,*sg0cof,**u,**v,*w,**cvm,chisq;
    float value,time,*afunc;
    int i;

if (ifa == 0)
    {
        ifa = 1;
```

Page 40

PATENT
NAVY CASE No. 78,988

```
        sig = vector(1,numsg0);
        sg0cof = vector(1,NLINR);
        u = matrix(1,numsg0,1,NLINR);
        v = matrix(1,NLINR,1,NLINR);
        w = vector(1,NLINR);
        cvm = matrix(1,NLINR,1,NLINR);

for (i=1;i<=numsg0;i++) sig[i] = 1.0/sqroot(sg0wgt[i]);

svdfit(sg0age,sg0pro,sig,numsg0,sg0cof,NLINR,u,v,w,&chisq,fpolyn);
        svdvar(v,NLINR,w,cvm);

free_matrix(u,1,numsg0,1,NLINR);
        free_matrix(v,1,NLINR,1,NLINR);
        free_vector(w,1,NLINR);
        free_matrix(cvm,1,NLINR,1,NLINR);
        free_vector(sig,1,numsg0);
    } if (tage <= sg0age[numsg0])
    {
        time = tage;
    }
    else
    {
        time = sg0age[numsg0];
    } afunc = vector(1,NLINR);
    fpolyn (time,afunc,NLINR);

value = 0.0e0;
    for (i=1;i<=NLINR;i++) value += sg0cof[i]*afunc[i];

free_vector(afunc,1,NLINR);

return (ktfunc(tage)*expten(value));

/* ------------------------------------------------------------------- */
/* Define function stbfcn                                              */
/* Use: the function computes the value of the stb parameter           */
/* Pre: the function is passed the current age                         */
/* Act: the function computes the value of the negative reciprocal of  */
/*      the slope of log corrected stress vs reduced time to failure   */
/*      curve by fitting a linear regression fit to the observed data; */
/*      on the first call the function computes the regression         */
/*      coefficients and on subsequent calls estimates the value of stb*/
/*      using the computed coefficients                                */
/* Pst: the function returns the computed value of stb                 */
/* ------------------------------------------------------------------- */
float stbfcn (tage)
float tage;
{
    static int ifb=0;
    static float *sig,*stbcof,**u,**v,*w,**cvm,chisq;
    float time,value,*afunc;
```

PATENT
NAVY CASE No. 78,988

```
    int i;

if (ifb == 0)
    {
        ifb = 1;
        sig = vector(1,numstb);
        stbcof = vector(1,NLINR);
        u = matrix(1,numstb,1,NLINR);
        v = matrix(1,NLINR,1,NLINR);
        w = vector(1,NLINR);
        cvm = matrix(1,NLINR,1,NLINR);

for (i=1;i<=numstb;i++) sig[i] = 1.0e0/sqroot(stbwgt[i]);

svdfit(stbage,stbpro,sig,numstb,stbcof,NLINR,u,v,w,&chisq,fpolyn);
        svdvar(v,NLINR,w,cvm);

free_matrix(u,1,numstb,1,NLINR);
        free_matrix(v,1,NLINR,1,NLINR);
        free_vector(w,1,NLINR);
        free_matrix(cvm,1,NLINR,1,NLINR);
        free_vector(sig,1,numstb);
    } if (tage <= stbage[numstb])
    {
        time = tage;
    }
    else
    {
        time = stbage[numstb];
    } afunc = vector(1,NLINR);
    fpolyn(time,afunc,NLINR);

value = 0.0e0;
    for (i=1;i<=NLINR;i++) value += stbcof[i]*afunc[i];

free_vector(afunc,1,NLINR);

return (value + stbran);
}

/* -------------------------------------------------------------------- */
/* Define function stress                                               */
/* Use: the function computes the corrected stress used by the damage   */
/*      model                                                           */
/* Pre: the function is passed the current time                         */
/* Act: the function computes the current temperature using the input   */
/*      temperature profile, the shifted stress free temperature, the   */
/*      relaxation moduli and then applies the regression fit parameters*/
/*      to compute the corrected stress                                 */
/* Pst: the function returns the value of the corrected stress          */
/* -------------------------------------------------------------------- */
float stress (tage)
float tage;
```

PATENT
NAVY CASE No. 78,988

```
{
    float ttemp,ttsf,tfactr,tbulk,tintf,ei,eb,en,em,str,tau,bulkcf,intfcf;

static int ifc=0;
    static float *smdcof,*xa,*ya,*sig,**u,**v,*w,**cvm,chisq;
    float *afunc;
    int i;

if (ifc == 0)
    {
        ifc = 1;
        sig = vector(1,numstr);
        xa = vector(1,numstr);
        ya = vector(1,numstr);
        smdcof = vector(1,NLINR);
        u = matrix(1,numstr,1,NLINR);
        v = matrix(1,NLINR,1,NLINR);
        w = vector(1,NLINR);
        cvm = matrix(1,NLINR,1,NLINR);

for (i=1;i<=numstr;i++)
        {
            xa[i] = ebspro[i]/eispro[i];
            ya[i] = sigpro[i]/eispro[i];
            sig[i] = 1.0/eispro[i];
        } svdfit(xa,ya,sig,numstr,smdcof,NLINR,u,v,w,&chisq,fpolyn);
        svdvar(v,NLINR,w,cvm);

free_matrix(u,1,numstr,1,NLINR);
        free_matrix(v,1,NLINR,1,NLINR);
        free_vector(w,1,NLINR);
        free_matrix(cvm,1,NLINR,1,NLINR);
        free_vector(xa,1,numstr);
        free_vector(ya,1,numstr);
        free_vector(sig,1,numstr);
    } ttemp = temper (tage);
    ttsf = tempsf (tage);
    tfactr = (ttsf - ttemp)/(tsfint - tempfe);
    atbulk = atblog (ttemp);
    atintf = atilog (ttemp);
    tau = timint/tau0;
    bulkcf = smdcof[2];
    intfcf = smdcof[1];

if (tau > TINY)
    {
        tbulk = (float) logten(tau) - atbulk;
        tintf = (float) logten(tau) - atintf;
    }
    else
    {
        tbulk = (float) logten(TINY) - atbulk;
        tintf = (float) logten(TINY) - atintf;
```

PATENT
NAVY CASE No. 78,988

```
    }
    ebulk = ebklog (tbulk);
    eintf = einlog (tintf);

en = blkage (tage, enmax, enlmb);
    em = intage (tage);
    eb = expten(ebulk);
    ei = expten(eintf);
    str = k3d*(bulkcf*en*eb + intfcf*em*ei)*tfactr;

return (str);
}
/* --------------------------------------------------------------- */
/*                                                                 */
/* Define function failpr                                          */
/* Use: the function computes the distribution function for the failure */
/*      probability based on the simulation results so that the upper   */
/*      confidence limit can be computed by the root finder        */
/* Pre: the function is passed the failure probability             */
/* Act: the function computes the confidence level that the true   */
/*      failure probability is less than the prescribed value assuming */
/*      a beta density and subtracts the desired confidence level for  */
/*      the root finder                                            */
/* Pst: the function returns the computed confidence level minus the   */
/*      the desired confidence level                               */
/* --------------------------------------------------------------- */
float failpr (x)
float x;
{
    return (betai(betap,betaq,x) - CONFID);
}

/* --------------------------------------------------------------- */
/*                                                                 */
/* Define function derivs                                          */
/* Use: the function computes the time-derivative of the damage function */
/* Pre: the function is passed the time and pointers to the independent */
/*      variable and derivative arrays                             */
/* Act: the function calls the stress function to compute corrected */
/*      stress at the prescribed time and then computes the damage */
/*      function time derivative                                   */
/* Pst: the function returns a pointer to the damage function derivative */
/*      to the ode integrator                                      */
/* --------------------------------------------------------------- */
void derivs (t, y, dydt)
float t,y[],dydt[];
{
    float sigma,sig0,sigi,strmod,stb,temp;

sig0 = sigma0(t);
    sigi = sigmai(t);
    sigma = stress(t);
    stb = stbfcn(t);

if ((sigma - sigi) > TINY*(sig0 - sigi))
    {
        strmod = (sigma - sigi)/(sig0 - sigi);
```

PATENT
NAVY CASE No. 78,988

```
        temp = stb*logten(strmod) - atintf;
        dydt[1] = expten(temp)/tau0;
    }
    else
    {
        dydt[1] = 0.0e0;
    }
}

/* ------------------------------------------------------------- */
/*                                                               */
/* Define function input                                         */
/* Use: the function opens and reads the given input filename for the */
/*      necessary input parameters                               */
/* Pre: the function is passed the name of the input filename   */
/* Act: the function opens the named file and reads the input values; */
/*      the function also allocates the necessary storage for the */
/*      input and output arrays                                  */
/* Pst: the function returns no value                            */
/* ------------------------------------------------------------- */
void input (filename)
char filename[80];
{
    int i,num;
    float intrvl,begage;
    FILE *fpi;

fpi = fopen(filename,"r");

fscanf(fpi,"%d %f %f %f", &num,&begage,&rlxtim,&tmpfrq);
    numpro = num + 1;

timpro = vector(1,numpro);
    tmppro = vector(1,numpro);
    tmpsig = vector(1,numpro);
    tmpran = vector(1,numpro);
    tmpamp = vector(1,numpro);
    tsftmp = vector(1,numpro);
    strpro = vector(1,numpro);
    ebkpro = vector(1,numpro);
    einpro = vector(1,numpro);
    dampro = vector(1,numpro);
    lsfpro = vector(1,numpro);
    rellim = vector(1,numpro);
    nfail  = ivector(1,numpro);

timpro[1] = begage;
    for (i=1;i<=num;i++)
    {
        fscanf(fpi,"%f %f %f %f",
                &intrvl,&tmppro[i],&tmpsig[i],&tmpamp[i]);
        timpro[i+1] = timpro[i] + intrvl;
        tmpran[i] = tmppro[i];
    }
    tmppro[numpro] = tmppro[num];
    tmpsig[numpro] = tmpsig[num];
    tmpamp[numpro] = tmpamp[num];
    tmpran[numpro] = tmppro[numpro];
```

Page 45

PATENT
NAVY CASE No. 78,966

```
tinitl = timpro[1];
tfinal = timpro[numpro];

fscanf(fpi,"%d", &numtsf);

timtsf = vector(1,numtsf);
tsfpro = vector(1,numtsf);

for (i=1;i<=numtsf;i++)
{
    fscanf(fpi,"%f %f", &timtsf[i],&tsfpro[i]);
} fscanf(fpi,"%f %f %f",&tsfint,&tsfamb,&sfrsig);
sfrran = 0.0e0;

fscanf(fpi,"%d", &numatb);

atbtmp = vector(1,numatb);
logatb = vector(1,numatb);
atbran = 0.0e0;

for (i=1;i<=numatb;i++)
{
    fscanf(fpi,"%f %f", &atbtmp[i],&logatb[i]);
} fscanf(fpi,"%d", &numati);

atitmp = vector(1,numati);
logati = vector(1,numati);
atiran = 0.0e0;

for (i=1;i<=numati;i++)
{
    fscanf(fpi,"%f %f", &atitmp[i],&logati[i]);
} fscanf(fpi,"%d", &numebk);

ebktat = vector(1,numebk);
logebk = vector(1,numebk);
ebkran = 0.0e0;

for (i=1;i<=numebk;i++)
{
    fscanf(fpi,"%f %f", &ebktat[i],&logebk[i]);
} fscanf(fpi,"%d", &numein);

eintat = vector(1,numein);
logein = vector(1,numein);
einran = 0.0e0;

for (i=1;i<=numein;i++)
```

Page 46

```
{
    fscanf(fpi,"%f %f", &eintat[i],&logein[i]);
} fscanf(fpi,"%d", &numkt);

ktage = vector(1,numkt);
ktpro = vector(1,numkt);
ktwgt = vector(1,numkt);
ktran = 0.0e0;

for (i=1;i<=numkt;i++)
{
    fscanf(fpi,"%f %f %f", &ktage[i],&ktpro[i],&ktwgt[i]);
} fscanf(fpi,"%f",&ktsig);

fscanf(fpi,"%d", &numstr);

sigpro = vector(1,numstr);
ebspro = vector(1,numstr);
eispro = vector(1,numstr);

for (i=1;i<=numstr;i++)
{
    fscanf(fpi,"%f %f %f", &eispro[i],&ebspro[i],&sigpro[i]);
} fscanf(fpi,"%f %f %f",&tempfe,&trefbk,&trefin);

fscanf(fpi,"%d",&numem);

emage = vector(1,numem);
empro = vector(1,numem);

for (i=1;i<=numem;i++)
{
    fscanf(fpi,"%f %f", &emage[i],&empro[i]);
} fscanf(fpi,"%f %f",&ebrtmu,&ebrtsg);
fscanf(fpi,"%f %f",&enmax,&enlmb);

ebrati = ebrtmu;

fscanf(fpi,"%f %f",&atbsig,&atisig);
fscanf(fpi,"%f %f",&ebksig,&einsig);
fscanf(fpi,"%f",&k3d);

fscanf(fpi,"%f",&strthr);
fscanf(fpi,"%f",&tau0);

fscanf(fpi,"%d", &numsg0);

sg0age = vector(1,numsg0);
sg0pro = vector(1,numsg0);
```

PATENT
NAVY CASE No. 78,968

```
    sg0wgt = vector(1,numsg0);

for (i=1;i<=numsg0;i++)
    {
        fscanf(fpi,"%f %f %f", &sg0age[i],&sg0pro[i],&sg0wgt[i]);
    } fscanf(fpi,"%d", &numstb);

stbage = vector(1,numstb);
    stbpro = vector(1,numstb);
    stbwgt = vector(1,numstb);
    stbran = 0.0e0;

for (i=1;i<=numstb;i++)
    {
        fscanf(fpi,"%f %f %f", &stbage[i],&stbpro[i],&stbwgt[i]);
    } fscanf(fpi,"%f",&stbsig);

fscanf(fpi,"%d %d",&numitr,&idum);

if (numitr > 0)
    {
        damsim = matrix(1,numitr,1,numpro);
    } close (fpi);
    return;
}

/* ---------------------------------------------------------------- */
/*                                                                  */
/* Define function damage                                           */
/* Use: the function computes the accumulated damage from tinitl to */
/*      tfinal                                                      */
/* Pre: the function is passed the current iteration number         */
/* Act: the function integrates the damage function from tinitl to  */
/*      tfinal to compute the accumulated damage at each temperature*/
/*      profile point and stores the data in the appropriate global */
/*      arrays                                                      */
/* Pst: the function returns no value                               */
/* ---------------------------------------------------------------- */
void damage (iter)
int iter;
{
    float *ystart,h1,hmin,ti,tf,logtat;
    int i,nok,nbad;

iterno = iter;
    timint = timpro[2] - timpro[1];

if (iter == 0)
    {
        tsftmp[1] = tempsf(timpro[1]);
        strpro[1] = stress(timpro[1]);
        ebkpro[numpro] = 0.0;
```

Page 48

PATENT
NAVY CASE No. 78,888

```
        einpro[numpro] = 0.0;
        dampro[1] = logten(TINY);
        lsfpro[1] = expten(-dampro[1]/stbfcn(timpro[1]));
        nfail[1] = 0;
        corran = 0.0;
    } ystart = vector(1,NVAR);
    for (i=1;i<=NVAR;i++) ystart[i] = 1.0e0;

for (i=1;i < numpro;i++)
    {
        ti = timpro[i];
        tf = timpro[i+1];
        timint = tf - ti;

h1 = tf - ti;
        hmin = 0.0e0;
        odeint (ystart,NVAR,ti,tf,EPSLON,h1,hmin,&nok,&nbad,derivs,rkqc);

if (iter == 0)
        {
            tsftmp[i+1] = tempsf(tf);
            strpro[i+1] = stress(tf);
            logtat = logten(timint/tau0) - atblog(tmpran[i]);
            ebkpro[i] = blkage(tf,enmax,enlmb)*expten(ebklog(logtat));
            logtat = logten(timint/tau0) - atilog(tmpran[i]);
            einpro[i] = intage(tf)*expten(einlog(logtat));
            if (ystart[1] > (1.0e0 + TINY))
                dampro[i+1] = logten(ystart[1] - 1.0e0);
            else
                dampro[i+1] = logten(TINY);
            lsfpro[i+1] = expten(-dampro[i+1]/stbfcn(tf));
            nfail[i+1]  = 0;
        }
        else
        {
            if (i == 1) damsim[iter][i] = logten(TINY);
            if (ystart[1] >= 2.0e0) nfail[i+1]++;
            if (ystart[1] > (1.0e0 + TINY))
                damsim[iter][i+1] = logten(ystart[1] - 1.0e0);
            else
                damsim[iter][i+1] = logten(TINY);
        }
    } free_vector(ystart,1,NVAR);
}

/* ------------------------------------------------------------------ */
/* Define function simult                                              */
/* Use: this function performs the Monte-Carlo simulation loop for the */
/*      damage analysis                                                */
/* Pre: the function is passed the number of iterations to perform     */
/* Act: the function computes the accumulated damage using the same    */
/*      values of the input parameters but varying the parameter       */
/*      values used in the computation for each iteration              */
```

PATENT
NAVY CASE No. 78,988

```
/*      the input temperature-time profile is varied with a distinct  */
/*      random deviate used at each time step                         */
/* Pst: the function returns no value                                 */
/* ---------------------------------------------------------------- */
void simult (iterat)
int iterat;
{
        int i,j;

for (i=1;i<=iterat;i++)
        {
            corran = gasdev(&idum);

for (j=1;j<=numpro;j++)
            {
                    tmpran[j] = tmppro[j] + gasdev(&idum)*tmpsig[j];
            }
            atbran = gasdev(&idum)*atbsig;
            atiran = gasdev(&idum)*atisig;
            sfrran = gasdev(&idum)*sfrsig;
            ebkran = gasdev(&idum)*ebksig;
            ebrati = ebrtmu + gasdev(&idum)*ebrtsg;
            einran = corran*einsig;
            ktran  = corran*ktsig;
            stbran = gasdev(&idum)*stbsig;

damage(i);

} for (i=1;i<=numpro;i++)
        {
            betap = nfail[i] + 1.0;
            betaq = numitr - nfail[i] + 1.0;
            rellim[i] = 1.0 - zbrent(failpr,0.0,1.0,EPSBRT);
        }

/* ---------------------------------------------------------------- */
/* Define function output                                            */
/* Use: this function prints the output to a file of the most likely */
/*      parameter values and the Monte Carlo simulation damage       */
/*      computation                                                  */
/* Pre: the function is passed the name of the output file and the   */
/*      number of Monte Carlo simulation iterations                  */
/* Act: the function opens the output file, then writes the output data */
/*      to the file and then closes the file                         */
/* Pst: the function returns no value                                */
/* ---------------------------------------------------------------- */
void output (filout,filsim,iter)
char filout[80],filsim[80];
int iter;
{
    int i,j;
    float mulogd,varlgd,prfail;
    FILE *fpo,*fps;
```

```
        fpo = fopen (filout,"w");
        fps = fopen (filsim,"w");

fprintf (fpo, "%s %s %s %s %s %s %s %s\n","    Time"," Temp",
            "Bulk Modul","Int. Modul","   Tsf"," Stress  ","Log(Dam)",
            "  OLFOS");

for (i=1;i<=numpro;i++)
        {
            fprintf (fpo,"%9.2f %6.1f %10.3e %10.3e %6.2f %10.3e %8.4f %8.4f\n",
                timpro[i],tmppro[i],ebkpro[i],einpro[i],tsftmp[i],strpro[i],
                dampro[i],lsfpro[i]);
        } close (fpo);

if (iter > 0)
        {
            fprintf (fps,"%s %6d \n","Number of iterations = ",iter);
            fprintf (fps,"%s %s %s %s %s\n","  Time   "," Mean log(dam)",
                " Var. log(dam)","  Prfail "," Rel. Limit");

for (j=1;j<=numpro;j++)
            {
                mulogd = 0.0e0;
                varlgd = 0.0e0;
                prfail = (float)(nfail[j])/numitr;

for (i=1;i<=iter;i++)
                {
                    mulogd += damsim[i][j]/numitr;
                }
                for (i=1;i<=iter;i++)
                {
                    varlgd += SQR((damsim[i][j] - mulogd))/numitr;
                } fprintf (fps,"%8.2f %14.4f %14.4f %10.6f %10.6f\n",
                    timpro[j],mulogd,varlgd,prfail,rellim[j]);
            } close (fps);
        }
}
/* ------------------------------------------------------------------ */
/* Define function main                                                */
/* ------------------------------------------------------------------ */
main ()
{
    printf ("Name of input file: >");
    sscanf (gets(keybuffer), "%s", infile);
    printf ("Name of regular output file: >");
    sscanf (gets(keybuffer), "%s", outfil);
    printf ("Name of simulation output file: >");
    sscanf (gets(keybuffer), "%s", simout);

input (infile);
```

PATENT
NAVY CASE No. 78,988

```
    damage (0);

if (numitr > 0) simult (numitr);

output (outfil,simout,numitr);

printf ("\nProgram terminating normally.\n");

printf ("\n                -*-*[ End of run ]*-*-             \n");

exit(0);
}
/* ============================================================== */
/* End of file                                                    */
/* ============================================================== */
```

What is claimed is:

1. A method for estimating damage to a filled polymeric material, comprising the steps of:

building a finite element model of the polymeric material structure;

identifying a high stress area of the polymeric material structure;

determining an expected range of a relaxation modulus of the polymeric material expected for a load history for the structure;

exercising the finite element model over discrete intervals for the expected relaxation modulus range;

determining regression coefficients for a fit of stress versus relaxation modulus for the high stress area;

determining the relaxation modulus history from the load history;

determining a stress history from the load history using the determined regression coefficients and the relaxation modulus history; and numerically integrating a damage function using the determined stress history.

2. The method of claim 1, said step of determining a stress history further comprising:

determining stress using the equation:

$$\sigma = K \sum_{i=1}^{N} (a_i E_{ni} E_i)(T_{SF} - T)/(T_{SF0} - T_0)$$

where $E_i$ are the relaxation moduli of regions comprising the structure; $E_{ni}$ are aging functions for determining the effect of aging of a material on the relaxation moduli; $a_i$ are the determined regression coefficients; K is a proportionality constant for adjusting for a modeling approximation; $T_{SF}$ is the stress-free temperature of the polymeric material; $T_{SF0}$ is the common stress-free temperature for which the $a_i$ were determined; $T_0$ is the common environmental temperature for which the $a_i$ were determined; and T is the temperature at which the stress $\sigma$ is being estimated.

3. The method of claim 1, said step of numerically integrating the damage function further comprising:

varying the value of a parameter used in evaluating the damage function according to a statistical distribution of the parameter; and repeating a number of iterations of the numerical integration, for performing a Monte Carlo simulation.

4. The method of claim 2, said step of numerically integrating the damage function further comprising:

varying the value of a parameter used in evaluating the damage function according to a statistical distribution of the parameter; and repeating a number of iterations of the numerical integration, for performing a Monte Carlo simulation.

5. The method of claim 3, said step of varying the value of a parameter comprising varying a load parameter.

6. The method of claim 3, said step of varying the value of a parameter comprising varying a material mechanical parameter.

7. The method of claim 5, said step of varying the value of a parameter comprising varying the value of the temperature.

8. The method of claim 6, said step of varying the value of a parameter comprising varying the value of the relaxation modulus.

9. The method of claim 6, said step of varying the value of a parameter comprising varying the value of the stress which will cause failure in a given time.

10. The method of claim 6, said step of varying the value of a parameter comprising varying the value of the damage function exponent.

11. The method of claim 3, said step of varying the value of a parameter further comprising:

using mean and standard deviation values of the parameter derived from lot acceptance data.

12. The method of claim 3, said step of varying the value of a parameter further comprising:

using mean and standard deviation values of the parameter derived from an experimentally determined aging curve for the parameter.

13. The method of claim 3, said step of varying the value of a parameter comprising use of a truncated normal distribution curve for the parameter.

14. The method of claim 1, said step of determining the relaxation modulus history further comprising:

modeling the relaxation modulus history as a step function.

15. The method of claim 1, said step of determining the relaxation modulus history further comprising:

modeling the relaxation modulus history as a trapezoidal step function.

16. The method of claim 3, further comprising the step of:

estimating the probability of failure as the ratio of the number of iterations in which the damage function is greater than unity to the total number of iterations.

17. The method of claim 1, said step of determining the stress history further comprising determining the stress history using an aging function for a material property.

18. The method of claim 17, further comprising the step of:

approximating the aging function from experimentally measured aging data assuming a constant value for ages older than the last measured datum.

19. The method of claim 1, said finite element model being a plane strain finite element model.

20. The method of claim 2, further comprising:

K being a stress-concentration factor for adjusting for the three-dimensional nature of the structure when a two-dimensional finite element model is used to determine the regression coefficients.

21. The method of claim 1, further comprising the step of:

performing the numerical integration on a personal workstation.

* * * * *